United States Patent [19]
Bristol et al.

[11] 4,450,164
[45] May 22, 1984

[54] IMIDAZO[1,2-A]PYRIDINES AND USE

[75] Inventors: James A. Bristol, Ann Arbor, Mich.; Chester Puchalski, Dover, N.J.

[73] Assignee: Schering Corporation, Madison, N.J.

[21] Appl. No.: 450,885

[22] Filed: Dec. 20, 1982

Related U.S. Application Data

[63] Continuation-in-part of Ser. No. 277,576, Jun. 26, 1981, abandoned, which is a continuation-in-part of Ser. No. 114,473, Jan. 23, 1980, abandoned.

[30] Foreign Application Priority Data

Jan. 13, 1981 [ZA] South Africa ........................ 81/0219
Jun. 21, 1981 [EP] European Pat. Off. ......... 82105411.1

[51] Int. Cl.³ .................. A61K 31/435; C07D 471/04
[52] U.S. Cl. ...................................... 424/256; 546/121
[58] Field of Search ......................... 546/121; 424/256

[56] References Cited

U.S. PATENT DOCUMENTS

| | | | |
|---|---|---|---|
| 3,701,780 | 10/1972 | Fisher | 424/250 X |
| 4,044,015 | 8/1977 | Kuhla | 424/263 X |
| 4,092,321 | 5/1978 | Bochis | 424/256 X |
| 4,221,796 | 9/1980 | Wade et al. | 424/256 |

Primary Examiner—Richard Raymond
Attorney, Agent, or Firm—Gerald S. Rosen; Bruce M. Eisen; Anita W. Magatti

[57] ABSTRACT

This invention relates to imidazo[1,2-a]pyridine derivatives which are useful in the treatment of peptic ulcer diseases.

42 Claims, No Drawings

IMIDAZO[1,2-A]PYRIDINES AND USE

This application is a continuation-in-part of our co-pending application Ser. No. 277,576, filed June 26, 1981, now abandoned, which is a continuation-in-part of Ser. No. 114,473, filed Jan. 23, 1980 and now abandoned.

SUMMARY OF THE INVENTION

This invention relates to certain substituted imidazo[1,2-a]pyridine compounds, pharmaceutical compositions thereof, novel processes and intermediates for making said compounds and methods of treating peptic ulcer disease utilizing said compounds.

More particularly, this invention relates to imidazo[1,2-a]pyridine compounds represented by the following structural formula

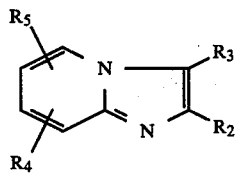

and the 2,3-dihydro, 5,6,7,8-tetrahydro and 2,3,5,6,7,8-hexahydro derivatives thereof and the pharmaceutical acceptable sales thereof, wherein:

$R_2$ is hydrogen, loweralkyl or hydroxyloweralkyl;
$R_3$ is lower alkyl, —$CH_2CN$, hydroxyloweralkyl, —NO, —$CH_2N=C$ or

(wherein $R_6$ and $R_7$ are independently selected from the group consisting of hydrogen and lower alkyl) or hydrogen provided $R_2$ is not hydrogen;
$R_4$ is Z-T-W wherein Z represents —O—, —NH— or a single bond; T represents a straight- or branched-chain lower-alkylene group; when Z is a single bond, T also represents an ethenylene or a propenylene group wherein the unsaturated carbon is at the single bond; when Z is —O—, T also represents an allylene group wherein the saturated carbon is at the oxygen; and W represents hydrogen, when T is allylene and Z is —O—, and Ar, wherein AR is selected from thienyl, pyridinyl, furanyl, phenyl and substituted phenyl wherein there are one or more substitutents on the phenyl independently selected from halogen or lower alkyl; and
$R_5$ is hydrogen, halogen or lower alkyl.

As employed throughout this specification, the term "halogen" means fluoro, chloro, bromo and iodo, with chloro and fluoro being preferred. The term "lower" as it modifies such radicals as alkyl means straight- or branched-chain radicals having up to six carbon atoms, e.g., methyl, ethyl, propyl, butyl, t-butyl, isopropyl, neopentyl, dimethylbutyl and the like. Methyl is the preferred lower alkyl.

"Pyridinyl" means the 2-, 3- and 4- isomers and their halogen- and lower alkyl- substituted analogs; "thienyl" means the 2- and 3-isomers and their halogen- and lower alkyl-substituted analogs; "furanyl" means the 2- and 3-isomers and their halogen- and lower alkyl-substituted analogs;

When "Ar" is phenyl, the substitutents can be in the meta, ortho and/or para positions of the phenyl. The preferred substitutents are halogen.

The $R_5$ substitutents can be on one or more of the 5-, 6-, 7- or 8-positions of the imidazo[1,2-a]pyridine nucleus not already substituted by an $R_4$ substitutent.

"Pharmaceutically acceptable salts" means salts wherein an acidic hydrogen forms an acid addition salt with an amine, e.g., the phosphate salt of 3-amino-2-methyl-8-phenylmethoxyimidazo-[1,2-a]pyridine. Suitable acids for the pharmaceutically acceptable acid addition salts include hydrochloric, sulfuric, phosphoric, nitric, acetic, propionic, maleic, ascorbic, citric and the like. The salts are prepared by procedures well known in the art.

A preferred subgroup of compounds of Formula I are those wherein $R_2$ represents methyl or ethyl; $R_3$ represents —$NH_2$, —$NHC_2H_5$, —$CH_2CN$, —$CH_3$, —$CH_2OH$ or —$CH_2N=C$; $R_4$ represents —$OCH_2Ar$, —$NHCH_2Ar$, —$CH=CH-(CH_2)_nAr$ or —$CH_2CH_2(CH_2)_nAr$ wherein n is zero or one and Ar is as defined hereinabove; and $R_5$ is hydrogen, fluoro, chloro or methyl.

A more preferred subgroup of compounds in wherein $R_4$ is at the 8-position and $R_5$, when other than hydrogen, is at the 7-position.

Most preferred are those compounds in which $R_4$ is at the 8-position and is selected from phenylmethoxy, phenylethyl, 3-phenyl-1-propenyl, phenylethenyl, benzylamino, 3-thienylmethoxy and 3-thienylmethanamino;
$R_2$ is methyl;
$R_3$ is amino, cyanomethyl or methyl; and
$R_5$ is hydrogen or methyl at the 7-position.

Examples of imidazo[1,2-a]pyridine compounds within the scope of this invention are:
1. 3-amino-2-methyl-8-(2-phenylethyl)imidazo-[1,2-a]pyridine;
2. 2,3-dimethyl-8-[(2-phenyl)ethenyl]imidazo[1,2-a]pyridine;
3. 3-cyanomethyl-2-methyl-8-(3-phenyl-1-propenyl)imidazo[1,2-a]pyridine;
4. 2,7-dimethyl-8-phenylmethoxyimidazo[1,2-a]pyridine-3-acetonitrile;
5. 3-ethylamino-2-methyl-8-phenylmethoxyimidazo[1,2-a]pyridine;
6. 3-ethylamino-2-methyl-8-(2-phenylethyl)-imidazo[1,2-a]pyridine;
7. 3-amino-2-methyl-8-phenylmethoxyimidazo[1,2-a]pyridine;
8. 3-amino-2-ethyl-8-phenylmethoxyimidazo[1,2-a]pyridine;
9. 3-amino-2,6-dimethyl-8-phenylmethoxyimidazo[1,2-a]pyridine;
10. 3-amino-2,7-dimethyl-8-phenylmethoxyimidazo[1,2-a]pyridine;
11. 3-amino-8-(2-fluorophenylmethoxy)-2-methylimidazo[1,2-a]pyridine;
12. 3-amino-8-(4-chlorophenylmethoxy)-2-methylimidazo[1,2-a]pyridine;
13. 3-amino-2-methyl-8-[(3-thienylethyl)amino]imidazo[1,2-a]pyridine;
14. 3-amino-2-methyl-8-(3-thienylmethoxy)imidazo[1,2-a]pyridine;

15. 3-amino-2-methyl-8-(2-thienylmethoxy)imidazo[1,2-a]pyridine;
16. 2-methyl-3-isocyanomethyl-8-phenylmethoxyimidazo[1,2-a]pyridine;
17. 2-methyl-8-[3-thienylmethylamino]-imidazo[1,2-a]pyridine-3-acetonitrile;
18. 2-methyl-6-(2-phenylethyl)-imidazo[1,2-a]pyridine-3-acetonitrile;
19. 3-amino-2-methyl-6-(2-phenylethyl)-imidazo[1,2-a]pyridine;
20. 3-amino-8-(4-fluorophenylmethoxy)-2-methylimidazo[1,2-a]pyridine;
21. 2-methyl-8-(2,4,6-trimethylphenylmethoxy)imidazo[1,2-a]pyridine;
22. 8-(3,4-dichlorophenylmethoxy)-2-methylimidazo[1,2-a]pyridine;
23. 8-(2-fluorophenylmethoxy)-2-methylimidazo[1,2-a]pyridine-3-acetonitrile;
24. 8-(4-fluorophenylmethoxy)-2-methylimidazo[1,2-a]pyridine;
25. 2-methyl-8-(2-phenylethyl)imidazo[1,2-a]pyridine;
26. 8-(4-chlorophenylmethoxy)-2-methylimidazo[1,2-a]pyridine;
27. 2-methyl-8-(2-thienylmethoxy)imidazo[1,2-a]pyridine-3-acetonitrile;
28. 2-methyl-8-(2-pyridylmethoxy)imidazo[1,2-a]pyridine-3-acetonitrile;
29. 8-(3,4-dichlorophenylmethoxy)-2-methylimidazo[1,2-a]pyridine-3-acetonitrile;
30. 8-(4-methoxyphenylmethoxy)-2-methylimidazo[1,2-a]pyridine-3-acetonitrile;
31. 8-(4-t-butylphenylmethoxy-2-methylimidazo[1,2-a]pyridine-3-acetonitrile;
32. 8-(4-chlorophenylmethoxy)-methylimidazo[1,2-a]pyridine-3-acetonitrile;
33. 8-(3,4-dichlorophenylmethoxy)-3-hydroxymethyl-2-methylimidazo[1,2-a]pyridine;
34. 8-(4-chlorophenylmethoxy)-3-hydroxymethyl-2-methylimidazo[1,2-a]pyridine;
35. 8-phenylmethoxy-2-ethylimidazo[1,2-a]pyridine;
36. 8-phenylmethoxyimidazo[1,2-a]pyridine-3-acetonitrile;
37. 8-phenylmethoxy-2-hydroxymethylimidazo[1,2-a]pyridine;
38. 3-hydroxymethyl-2-methyl-8-(2-phenylethoxy)imidazo[1,2-a]pyridine;
39. 8-phenylmethoxy-2,3-dimethylimidazo[1,2-a]pyridine;
40. 2-methyl-8-(2-phenylethoxy)imidazo[1,2-a]pyridine-3-acetonitrile;
41. 2-methyl-8-(1-phenylethoxy)imidazo[1,2-a]pyridine-3-acetonitrile;
42. 2-methyl-8-(2-phenylethyl)imidazo[1,2-a]pyridine-3-acetonitrile;
43. 3-hydroxymethyl-2-methyl-8-(2-phenylethyl)imidazo[1,2-a]pyridine;
44. 2-methyl-8-(3-phenylpropoxy)imidazo[1,2-a]pyridine-3-acetonitrile;
45. 8-phenylmethoxy-2-isopropylimidazo[1,2-a]pyridine-3-acetonitrile;
46. 8-phenylmethoxy-2-ethylimidazo[1,2-a]pyridine-3-acetonitrile;
47. 8-benzylamino-2,3-dimethylimidazo[1,2-a]pyridine;
48. 8-phenylmethoxy-2-methylimidazo[1,2-a]pyridine-3-acetonitrile;
49. 8-phenylmethoxy-3-hydroxymethyl-2-methylimidazo[1,2-a]pyridine;
50. 3-hydroxymethyl-8-(2-fluorophenylmethoxy)-2-methylimidazo[1,2-a]pyridine;
51. 8-(4-t-butylbenzyloxy)-3-hydroxymethyl-2-methylimidazo[1,2-a]pyridine;
52. 8-(2-fluorophenylmethoxy)-2-methylimidazo[1,2-a]pyridine-3-acetonitrile;
53. 8-(4-fluorophenylmethoxy)-2-methylimidazo[1,2-a]pyridine-3-acetonitrile;
54. 2-methyl-8-(2,4,6-trimethylphenylmethoxy)imidazo[1,2-a]pyridine-2-acetonitrile;
55. 8-benzylamino-2-methylimidazo[1,2-a]pyridine-3-acetonitrile;
56. 2-methyl-8-(3-thienylmethoxy)imidazo[1,2-a]pyridine-3-acetonitrile;
57. 2-methyl-8-phenylmethoxyimidazo[1,2-a]pyridine;
58. 8-allyloxy-2-methylimidazo[1,2-a]pyridine-3-acetonitrile;
59. 2-ethyl-8-phenylmethoxyimidazo[1,2-a]pyridine-3-acetonitrile;
60. 2-ethyl-3-methyl-8-phenylmethoxyimidazo[1,2-a]pyridine;
61. 3-amino-2-methyl-8-phenylmethoxyimidazo[1,2-a]pyridine and the phosphate acid addition salt thereof;
62. 2-methyl-8-(3-phenylpropyl)imidazo[1,2-a]pyridine-3-acetonitrile;
63. 2-methyl-6-benzylaminoimidazo[1,2-a]pyridine-3-acetonitrile;
64. 2-methyl-6-phenylmethoxyimidazo[1,2-a]pyridine-3-acetonitrile;
65. 2-methyl-5-benzylaminoimidazo[1,2-a]pyridine-3-acetonitrile;
66. 2-methyl-5-phenylmethoxyimidazo[1,2-a]pyridine-3-acetonitrile;
67. 2,3-dimethyl-5-phenylmethoxyimidazo[1,2-a]pyridine;
68. 2-methyl-7-phenylmethoxyimidazo[1,2-a]pyridine-3-acetonitrile:

It is apparent that the compounds of this invention may be named in different ways. Thus, "benzyloxy" and "phenylmethoxy" are synonomous as are "cyanomethyl" and "acetonitrile". Therefore, as used herein, the names are interchangeable.

DETAILED DESCRIPTION OF THE INVENTION

In the preparation of the compounds of this invention (I), the nature and positioning of the substituents which are attached to the imidazo[1,2-a]pyridine nucleus preclude the convenience of having a single generic pathway by which all the compounds of this invention may be prepared. Instead, the nature of the substituents dictate the application of known chemical reactions performed in a variety of sequences to efficiently prepare any particular specific compound or subgeneric group of compounds embraced within the scope of this invention. Thus in describing the preparation of the compounds of this invention, it is convenient to state that the majority of the substituted imidazo[1,2-a]pyridine compounds of this invention are prepared by chemical transformations on a prepared imidazo[1,2-a]pyridine. These chemical transformations are analogously known chemical reactions which are effected in a sequence dictated by the compounds available as starting materials, as well as the nature of the substitents of the desired compound. The chemical reactions and the sequences in which they may be employed in the hereinafter transformations are illustrated in the hereinafter described examples. Modifications to prepare the desired compounds of this invention using the techniques well-known in the art will be apparent to those of ordinary skill in the art.

Most conveniently, the imidazo[1,2-a]pyridine starting compounds are prepared by a chemical condensation reaction of a 2-amino-3-arylalkoxypyridine with a reactive halogenated aldehyde, ketone, acid, ester or amide. In effecting this chemical condensation the reactants are heated together, preferably at 50° C. to 150° C. either neat or in a non-reactive anhydrous solvent under either basic or neutral conditions. The selection of the particular reactants for these condensations is illustrative of the types of choices available. For example, condensation of the 2-amino-3-arylalkoxypyridine with chloroacetaldehyde produces an imidazo[1,2-a]pyridine having an arylalkoxy moiety at its 8-position, and hydrogen at each of the 2- and 3-positions, which compounds are useful as intermediates in preparing biologically active compound of formula I. Condensation with chloroacetone produces an 8-arylalkoxyimidazo[1,2-a]pyridine having a methyl substituent at its 2-position, and hydrogen at its 3-position. Condensation with ethyl-2-chloroacetoacetate produces and 8-arylalkoxyimidazo[1,2-a]pyridine having a methyl substituent at it 2-position and an ethyl carboxylate substituent at its 3-position. Condensation with ethylbromopyruvate produces an 8-arylalkoxyimidazo[1,2-a]pyridine having hydrogen at its 3-position and an ethyl carboxylate substituent at its 2-position. Condensation with α-chloroacetic acid produces an 8-aryloxyimidazo[1,2-a]pyridine having hydrogen at its 3-position and a hydroxy group at its 2-position.

Analogously, condensation of the foregoing ketones, aldehydes, acids, esters and amides with modified 2-aminoarylalkoxypyridines (e.g., X-substituted-2-aminoarylalkoxypyridines) will produce the corresponding X-substituted-8-arylalkoxyimidazo[1,2-a]pyridines.

Use of a modified 2-amino-3-arylalkoxy pyridine in the chemical condensation results in a corresponding modified imidazo[1,2-a]pyridine. For example, use of a 2-amino-3-arylalkylpyridine produces an imidazo[1,2-a]pyridine wherein "Z" (of Formula I) is a bond connecting "T-W" (of formula I) at the 8-position thereof. Similarly, the preparation of the dihydro, tetrahydro and hexahydro derivatives are effected in accordance with well-known reduction techniques amply exemplified in this specification.

The preferred 2-lower alkylsubstituted-3-acetonitrile imidazo[1,2-a]pyridine can be prepared, for example, by transforming 8-hydroxy-2-methylimidazo[1,2-a]pyridine to the desired corresponding 2-methyl-8-phenylalkoxyimidazo[1,2-]pyridine by standard alkylation procedures wherein the reactants (e.g. benzylhalide and 8-hydroxy-2-methylimidazo[1,2-a]pyridine are heated together in the presence of a base (e.g. sodium hydride) and an organic solvent (e.g. dimethylformamide). The so-formed 2-methyl-8-phenylalkoxyimidazo[1,2-a]pyridine is then aminoalkylated using standard techniques such as by refluxing the imidazo[1,2-a]pyridine with an amine, e.g. dimethylamine hydrochloride, and paraformaldehyde, with or without an acid catalyst. The corresponding imidazo[1,2-a]pyridine bearing a dimethylaminomethyl substituent at its 3-position is then quaternized (by reaction with an alkyl halide, e.g. methyl iodide, dimethylsulfate, and the like) in an organic solvent such as acetone or ethanol and the resulting quaternary salt is subjected to a displacement reaction wherein the dimethylaminomethyl methiodide moiety is transformed to acetonitrile. This displacement reaction is effected by standard techniques such as by heating the intermediate imidazo[1,2-a]pyridine with an alkali metal cyanide (e.g. sodium cyanide) in the presence of a solvent (e.g. DMSO, ethanol or DMF). Obtention of other desired nitriles can be achieved with analogous transformations.

In the foregoing reaction, the 2-methyl-8-phenylalkoxyimidazo[1,2-a]pyridine having a dimethylaminoethyl group at C-3 may be quaternized by groups wherein the quaternary anion is a non-nucleophilic counter ion such as $BF_{-4}$, $PF_{-4}$, $CF_3SO_{-3}$, $FSO_{-3}$, etc. When the quaternary anion is a non-nucleophilic counter ion, the displacement reaction may also be carried out in an aqueous solvent (e.g. acetonitrile/water). Additionally, one may carry out the displacement reactions in the presence of a crown ether.

Alternatively, the desired compounds bearing a acetonitrile substituent at the 3-position can be prepared from an imidazo[1,2-a]pyridine bearing a hydroxymethyl substituent at the 3-position, e.g. 3-hydroxymethyl-8-phenylmethoxyimidazo[1,2-a]pyridine. In effecting this transformation, the imidazo[1,2-a]pyridine is first reacted with excess phosphoryl chloride to produce the corresponding 3-chloromethyl analog which substituent is converted to the desired acetonitrile by reaction with an alkali metal cyanide in the presence of an organic solvent (e.g. DMSO or acetonitrile).

Alternatively, condensation of an appropriate 2-amino-3-arylmethoxypyridine with an $R_2$—COCH(Cl)CH$_2$CN reactant (wherein $R_2$ is as previously defined except that, as is well known in the art, certain of the substituents must bear a removable protecting group, e.g. when $R_2$ is hydrloxyloweralkyl the hydroxy function is protected by esterification and the ester group is removed when the condensation reaction is completed affords the imidazo[1,2-a]pyridine-3-acetonitrile. For example, reaction of 2-amino-6-methyl-3-phenylmethoxypyridine with 3-chloro-4-oxopentanonitrile in ethanol in the presence of triethylamine affords, 2,5-dimethyl-8-phenylmethoxyimidazo[1,2-a]pyridine-3-acetonitrile.

Preparation of the key intermediates involved in the preparation of the desired imidazo[1,2-a]pyridine represents a unique and preferred process. This process involves the reaction of an appropriately substituted 2-amino-3-hydroxypyridine with an arylalkyl halide under phase-transfer catalytic conditions to afford a 2-amino-3-arylalkoxypyridine. The reaction is generally effected by admixing the reactants at or below room temperature in a mixture of water-immiscible organic solvent and aqueous hydroxide (preferably 40–50% sodium hydroxide) in the presence of 1 mole percent of a phase-tranfer catalyst, preferably methyltrialkyl ($C_8$–$C_{10}$) ammonium chloride (e.g. Adogen 464).

In general, in preparing compounds of formula I wherein Z represents —O—, —NH— or a single bond, the following process (A) may be used. A.

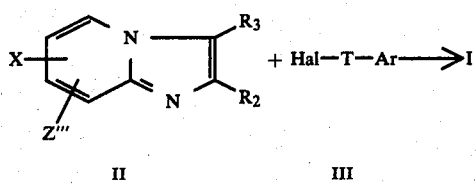

II                    III

In the above Formulae II and III, Hal represents Br, Cl or I; Z''' represents hydrogen, halogen (Cl, Br, I), —OH, or —NH₂; and R₅, R₂, R₃, T and Ar are above defined.

The reactants are heated together under standard reaction conditions known from the preparation of similar compounds, e.g. in an inert solvent in the presence of a base. When Z''' represents halogen, a copper catalyst is preferably used. When Z''' represents —OH or —NH₂, the reaction may be carried out with or without such copper catalyst.

8-Formylimidazo[1,2-a]pyridine having R₂ and R₃ substituents as defined hereinabove, upon reduction with sodium borohydride is converted to the corresponding 8-hydroxymethyl derivative, an intermediate for preparing compounds of formula I. Etherification of the 8-hydroxymethyl intermediate, e.g. by treatment with sodium hydride followed by reaction of the resulting sodium salt with an aralkyl halide, produces an 8-arylalkoxymethyl derivative. Alternatively, replacement of the hydroxyl group with a good leaving group (e.g. tosyl) followed by displacement thereof with an aryloxy alkali metal salt (e.g. sodium phenoxide) produces an 8-aryloxymethyl derivative of formula II.

An imidazo[1,2-a]pyridine having a formyl group at one of positions 5, 6, 7 or 8 is also a useful intermediate in introducing substituents of formula II. Thus, for example, reaction of 8-formylimidazo[1,2-a]pyridine having R₂ and R₃ functions as defined hereinabove with an arylamine or an aralkylamine followed by reduction of the resulting imines produces 8-arylaminoethyl- and 8-aralkylaminomethyl derivatives.

Compounds of this invention having an olefinic functionality at C-5, -6, -7 or 8, i.e. compounds of formula I wherein Z is a bond and T is an unsaturated lower alkylene, are derived from the corresponding formylimidazo[1,2-a]pyridine having R₂ and R₃ functions as defined hereinabove, upon reaction thereof under Wittig conditions or modifications thereof.

The starting compounds in the above reaction (A) are either known or may be obtained according to standard procedures, some of which are exemplified hereinafter.

As is obvious to anyone skilled in the art, numerous standard reactions may be applied for transferring one type of substituent R₂ and/or R₃ into another type. Thus, for example, for preparing compounds of Formula I wherein R₃ represents the group —CH₂CN, the following processes may be applied:

1. A compound of Formula I wherein R₂, R₅, T, Z and Ar are as defined for Formula I and R₃ represents either of the groups —CH₂CONH₂ and

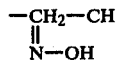

is subjected to a dehydration. The reaction is carried out by treating the starting compounds with a suitable dehydrating agent in an inert solvent, preferably at reduced temperatures. Preferred dehydrating agents are (CF₃CO)₂O (in pyridine), SeO₂ (in trichloromethane), POCl₃, etc. The starting compounds may be obtained according to standard procedures, e.g., as indicated hereinabove as and exemplified hereinafter.

2. A compound of Formula I wherein R₂, R₅, T, Z and Ar are as defined for formula I and R₃ represents the group

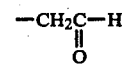

is treated with a suitable cyanocompound, e.g. Tosyl—CH₂—CN in the presence of potassium-t-butoxyde whereby the formyl function is replaced by CH₂CN.

3. A compound of Formula I wherein R₂, R₅, T, Z and Ar are as defined for formula I and R₃ represents the group —CH₂COOR (ester) is treated with a suitable amine, e.g. dimethylaluminum-amine resulting in a compound where R₃ is —CH₂CN.

4. A compound of Formula I wherein R₂, T, Z and Ar are as defined for Formula I and R₃ represents the group

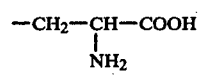

is treated with NaOCl under standard conditions.

5. A compound of Formula I wherein R₂, R₅, T, Z and Ar are as defined for Formula I and R₃ represents a group —CH₂CH₂NO₂ is subjected to a reductive dehydration, e.g. with PCl₃ and the like in pyridine to give the desired nitrile. [See J. Org. Chem. 42, 3956 (1977)].

6. A compound of Formula I wherein R₂, R₅, T, Z and Ar are as defined for Formula I and R₃ represents H is reacted with a compound of the Formula Hal—CH₂—CN wherein Hal is chloride or bromide in the presence of a Lewis acid (e.g. aluminium chloride, zinc chloride, boron chloride, etc.) or a phase transfer catalyst.

7. A compound of Formula I wherein R₂, R₅, T, Z and Ar are as defined for Formula I and R₃ represents the group

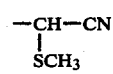

is subjected to a reduction, preferably with Raney-nickel whereby the —SCH₃—group is replaced by a hydrogen atom. The starting compound by be obtained by reacting a compound of Formula I wherein R₃ represents hydrogen with CH—3—S—CH(Cl)CN by means of a Friedel Crafts catalyst (e.g. SnCl₄, TiCl₄, AlCl₃, etc.)

In addition to modifying various R₃ groups into —CH₂CN groups as described in the above reactions, other transformations may be carried out, e.g. as indicated in Table I.

TABLE I

| STARTING R₃ | CHEMICAL REACTION | RESULTING R₃ |
|---|---|---|
| —COOC$_2$H$_5$ | reduction (LiAlH$_4$) | —CH$_2$OH |
| —CH$_2$NH$_2$ | 1. reaction with methyliodide 2. followed by reaction with metal cyanide | —CH$_2$CN |
| H | nitration (HNO$_3$/Acetic Acid) | —NO$_2$ |
| H | nitrousation | —NO |
| —N—(O)$_n$ | reduction (Zn/Acetic Acid) | —NH$_2$ |

(n = o,1)

The various substituents of R$_2$ may, where appropriate, be transferred into other R$_2$-substituents by reactions such as those outlined for R$_3$ in the processes described in Table I.

It is obvious to anyone skilled in the art that the sequence of certain reactions may be altered. Thus, for example, one may, in accordance with methods described herein, first prepare a compound of the formula II shown.

The following examples illustrate the preparations of compounds of this invention:

EXAMPLE 1

8-Benzyloxy-2-methyl-imidazo[1,2-a]pyridine

STEP A: Preparation of 2-amino-3-benzyloxypyridine

In a 12 liter 3-neck round bottom flask equipped with a mechanical stirrer and thermometer there were placed 2.5 liters of 40% sodium hydroxide solution, 26.5 g of Adogen 464 (Reg. Trademark) and 2.5 liters of dichloromethane. To this vigorously stirred mixture was added 550 g of 2-amino-3-hydroxypyridine. The temperature was 38° C. The brown orange mixture was cooled to 25° C., and 677.5 g of benzylchloride was added in one portion, stirred 16 hr. and the mixture was allowed to separate into 2 phases. The lower aqueous phase was separated and diluted with 1 liter of ice:water. This solution was then extracted with dichloromethane (3×15 liters). The combined dichloromethane extracts were added to the original dichloromethane phase, washed with 1 liter of saturated sodium chloride solution and dried over potassium carbonate. The dichloromethane extract was filtered and concentrated on the rotary evaporator to an orange solid. This solid was dissolved in 1 liter of boiling absolute ethanol, and the solution was filtered. The filtrate was chilled, and the crystals that formed were filtered, washed with 500 ml of ethanol at −10° C., and dried at 50° C. in a vacuum oven, to give the desired product.

In a similar manner, reaction of 2-amino-3-hydroxypyridine with the appropriate benzylhalide leads to the following aminopyridines:

2-amino-3-(3-trifluoromethylbenzyloxy)pyridine, 2-amino-3-(4-chlorobenzyloxy)pyridine,
2-amino-3-(4-fluorobenzyloxy)-pyridine,
2-amino-3-(4-t-butylbenzyloxy)-pyridine,
2-amino-3-(2-phenylethoxy)-pyridine and
2-amino-3-(3,4-dichlorobenzyloxy)-pyridine.

STEP B: Preparation of title compound.

Into a 12 liter 3 necked flask equipped with a mechanical stirrer and condenser, were placed 750 g of 2-amino-3-benzyloxy-pyridine (obtained according to Step A), 6.75 liters of absolute ethanol (one may also use methanol 3 liters) and 360 ml of chloroacetone. The solution was heated under reflux for 4 hrs.

An additional 180 ml of chloroacetone was added and the dark solution was heated under reflux for 18 hrs. The solvent was evaporated off and the residual dark oil was dissolved in 7 liters of water. The resulting solution was made strongly basic with 15% of sodium hydroxide and the basified solution was extracted with several portions (4×1.5 liters) of dichloromethane. The extracts were combined and washed with brine and the washed extracts evaporated down to a dark gum which was boiled with 7 liters of diisopropyl ether. The solution was decanted from insoluble material through a glass wool plug, and the filtrate was chilled. The resulting crystals were filtered and washed with cold diisopropyl ether. Recrystallization provided the pure product of this example (mp 93°–95° C.).

Similarly, reaction of the appropriate 2-amino-3-arylalkyloxypyridine (which may be synthesized from 2-amino-3-hydroxypyridine according to the procedures in Acta. Chem. Scand., 23, 1791 (1969).) and chloroacetone leads to the following imidazo[1,2-a]-pyridines:

8-(4-fluorobenzyloxy)-2-methylimidazo[1,2-a]pyridine,
8-(3,4-dichlorobenzyloxy)-2-methylimidazo[1,2-a]pyridine and 8-(4-chlorobenzyloxy)-2-methylimidazo[1,2-a]pyridine.

EXAMPLE 2

8-Benzyloxy-3-cyanomethyl-2-methylimidazo[1,2-a]pyridine

STEP A: Preparation of 3-chloro-4-oxopentanonitrile.

Into a 1-neck, 3 l round bottom flask there were placed 1 l diethylether (Et$_2$O) and 100 g 4-oxopentanonitrile. The magnetically stirred solution was cooled to 0°–5°, one drop HCl/Et$_2$O added, and 185 ml 97% of SO$_2$Cl$_2$ previously chilled to 5°–10° was added all at once. The ice bath was removed, and the pale greenish-yellow solution was warmed to 20±1° C. over 5 min. by a hot water bath. The temperature was maintained at 20±° C. by a cold water bath for 2½ hr. The pale yellow solution was evaporated on a rotary evaporator in a 30° water bath at 80 mm vacuum, and carefully watched. Near the end of solvent removal, the instant the near-colorless residue began to turn orange, the flask was removed quickly and diluted with 1 l cold Et$_2$O. One ml SO$_2$Cl$_2$ was added and stirred 15 min., and the orangish solution was diluted with 1 l cold Et$_2$O.

The ether solution was washed with 1 l cold saturated NaHCO$_3$-solution which was in turn extracted with 2×1 cold CH$_2$Cl$_2$. The CH$_2$Cl$_2$ was evaporated, the residue dissolved in 200 ml Et$_2$O, and added to the bicarbonatewashed ether solution. The ether was extracted by 2×1 l cold 10% NaHSO$_3$-solution and discarded. The bisulfite solution was cooled in an ice bath and 25% NaOH was added slowly to attain pH 7 (ca. 100 ml), 100 g NaHCO$_3$ was added to saturate the solution, and it was extracted with 5×1 l CH$_2$Cl$_2$; 25 g K$_2$CO$_3$ was added followed by extraction with 1 l CH$_2$Cl$_2$, and this was repeated with another 25 g K$_2$CO$_3$—1 l CH$_2$Cl$_2$. The combined extracts were dried over MgSO$_4$, and evaporated to leave a brown-orange oil, estimated from pmr to contain 3-Cl isomer, 5-Cl isomer, some unknown compounds and CH$_2$Cl$_2$.

Distillation of this oil through a jacketed 15-cm Vigreux column at 0.3 mmHg gave 3-chloro-4-oxopentanonitrile (b.p. 83°–93°).

STEP B: Preparation of title compound.

A solution of 0.86 g. of 3-chloro-4-oxopentanonitrile, 0.92 g. of 2-amino-3-phenylmethoxypyridine and 0.5 ml. of triethylamine in 15 ml. of ethanol was stirred for 16 hours, then concentrated to remove the triethylamine and ethanol. The residue was dissolved in methylene chloride and washed with water. The methylene chloride was concentrated and the residual oil was dissolved in 20 ml. of boiling acetonitrile, filtered, cooled, and treated with hydrogen chloride/methanol with cooling to give 0.22 g. of the desired product (m.p. 163°–166° C.).

EXAMPLE 3

8-(4-Fluorobenzyloxy)-2-methyl-imidazo[1,2-a]pyridine

STEP A: Preparation of 8-hydroxy-2-methyl-imidazo-[1,2-a]pyridine.

A mixture of 2-amino-3-hydroxypyridine (1,000 g) and chloroacetone (845 g) in 7.57 liters of ethanol was heated under reflux for 20 hrs. Most of the ethanol was removed by distillation and the residual material was dissolved in 7.57 liters of water. This solution was extracted four times with 1.2 liter portions of dichloromethane. The combined extracts were washed with 1 liter of water and this was combined with the aqueous solution. This solution was then adjusted to pH 11.5–12 with 850 ml of 50% sodium hydroxide. This basic solution was extracted three times with 1.2 liters of dichloromethane. The combined dichloromethane extracts were washed with 1 liter of $H_2O$ and this was added to the basic solution. This solution was chilled in an ice bath and the pH adjusted to 7 with 1.45 liters of 6 N hydrochloric acid. After standing overnight, the product was collected, washed with water, and dried. The product was recrystallized from dichloromethane/methanol to give the intermediate.

STEP B: Preparation of the title compound.

To a stirred suspension under nitrogen of 15.0 g 8-hydroxy-2-methyl-imidazo[1,2-a]pyridine (from Step A) in 150 ml dimethylformamide maintained at 0°–5° C., was added 5.15 g 50% sodium hydride-oil dispersion in portions over 10 minutes. The mixture was stirred in the cold ½ hr. and a brown solution resulted. 15.3 g 4-Fluorobenzyl chloride was added, and the solution was heated on a steam bath for ½ hr. The solution was poured into an ice bath and after ½ hour it became a brown solution. The solution was poured into 1.5 liters ice/water with vigorous stirring and the precipitate was separated by suction filtration, washed, and dried to give 8-(4-fluorobenzyloxy)-2-methylimidazo[1,2-a]pyridine (m.p. 137° C.).

By using appropriately substituted benzyl chlorides in the above reaction the following compounds are obtained:

8-(2-fluorobenzyloxy)-2-methylimidazo[1,2-a]pyridine;
8-(4-chlorobenzyloxy)-2-methylimidazo[1,2-a]pyridine;
8-(3,4-dichlorobenzyloxy)-2-methylimidazo[1,2-a]pyridine;
8-(2,6-dimethylbenzyloxy)-2-methylimidazo[1,2-a]pyridine;
2-methyl-8-(2,4,6-trimethylbenzyloxy)imidazo[1,2-a]pyridine; and
8-(2,6-difluorobenzyloxy)-2-methylimidazo[1,2-a]pyridine.

EXAMPLE 4

8-Benzylamino-3-cyanomethyl-2-methylimidazo[1,2-a]pyridine

STEP A: Preparation of 2-amino-3-benzylaminopyridine.

A mixture of 2,3-diaminopyridine (45 g), ethanol (500 ml), triethylamine (42 g) and benzyl bromide (70.5 g) was stirred at room temperature for 3 days. The solvent was evaporated in vacuo and the residue partitioned between chloroform (500 ml) and water (400 ml). The organic layer was eparated, filtered through a silica gel plug and evaporated in vacuo. The residue was triturated with hot chlorobutane to yield a brown powder.

STEP B: Preparation of title compound.

2-amino-3-benzylaminopyridine (17.6 g) obtained according to Step A, 3-chloro-4-oxopentanonitrile (11.6 g) and methanol (500 ml) were stirred together at room temperature for about 1 day. The methanol was then evaporated in vacuo and the residue partitioned between 1 N NaOH (350 ml) and ethyl acetate (500 ml) and the organic layer was separated, dried over $Na_2CO_3$ and evaporated. Chromatography on silica gel using $CHCl_3$ yielded a brown oil which was dissolved in ether (700 ml). Ethereal HCl was added and the HCl-salt of the desired product precipitated. Recrystallization from methanol gave the pure HCl salt.

EXAMPLE 5

8-(2-Fluorobenzyloxy)-3-hydroxymethyl-2-methylimidazo[1,2-a]pyridine

STEP A: Preparation of 8-(2-Fluorobenzyloxy)-2-methylimidazo[1,2-a]pyridine-3-carboxylic acid ethyl ester.

A mixture of 25.0 g of 2-amino-3-(2-fluorobenzyloxy)pyridine, 20.5 g ethyl 2-chloroacetoacetate, 10.0 g of sodium bicarbonate and 250 ml dimethoxyethane was heated under reflux for 48 hrs. An additional 5.0 g ethyl 2-chloroacetonacetate was added and refluxed for another 24 hrs., followed by another 5.0 g and refluxed for a further 66 hrs. The mixture was cooled and suctionfiltered. The solids collected were washed with tetrahydrofuran, and the combined filtrate and washings were evaporated in vacuo to leave a dark-colored oil. Hexane (200 ml) was added to the oil with vigorous stirring, and the resulting precipitate filtered off. To this solid was added (with vigorous stirring) acetonitrile (50 ml) and diisopropyl ether (200 ml) and stirring was continued for 0.5 hr. The suspended solid was filtered and crystallized from acetonitrile to give the desired ester.

Substitution of 2-amino-3-(2-phenylethoxy)pyridine, 2-amino-3-(4-fluorobenzyloxy)-pyridine; 2-amino-3-(4-chlorobenzyloxy)-pyridine; 2-amino-3-(2-pyridinylmethoxy)-pyridine; and 2-amino-3-benzyloxypyridine for the 2-amino-3-(2-fluorobenzyloxy)-pyridine and by substantially following the same procedure, the ethyl esters of the following compounds are produced:

8-(4-chlorobenzyloxy)-2-methylimidazo[1,2-a]pyridine-3-carboxylic acid,
8-(4-fluorobenzyloxy)-2-methylimidazo[1,2-a]pyridine-3-carboxylic acid,
2-methyl-8-(2-phenylethoxy)imidazo[1,2-a]pyridine-3-carboxylic acid,
2-methyl-8-(2-pyridyl-methoxy)imidazo[1,2-a]pyridine-3-carboxylic acid, 2-methyl-8-benzyloxyimidazo[1,2-a]pyridine-3-carboxylic acid, STEP B: Preparation of title compound.

To an ice-cooled suspension of 1.56 g of lithium aluminium hydride in 200 ml tetrahydrofuran (THF) there was added 15.0 g of 8-(2-fluorobenzyloxy)-2-methylimidazo[1,2-a]pyridine-3-carboxylic acid ethyl ester in portions so that the temperature remained below 10° C. After stirring at 0°–5° C. for an additional 1 hr., 1.6 ml water was added dropwise at 0°–10° C., followed by 1.6 ml 15 % aqueous sodium hydroxide and then 4.8 ml water. The mixture was allowed to warm to room temperature with stirring, and was then suction-filtered in a sintered glass funnel. The solids left in the funnel were thoroughly washed with 200 ml hot tetrahydrofuran and 4×150 ml hot chloroform. The filtrate and washings were combined, evaporated in vacuo, and the solid residue crystallized from acetonitrile to give the desired compound (m.p. 151°–153° C.).

By using the appropriate imidazo[1,2-a]pyridine-3-carboxylic acid ethyl esters and by substantially following the procedure of Step B, the following compounds are obtained:

8-(4-chlorobenzyloxy)-3-hydroxymethyl-2-methylimidazo[1,2-a]pyridine;

8-(4-fluorobenzyloxy)-3-hydroxymethyl-2-methylimidazo[1,2-a]pyridine;

3-hydroxymethyl-2-methyl-8-(2-phenylethoxy)imidazo[1,2-a]pyridine;

8-benzyloxy-3-hydroxymethyl-2-methylimidazo[1,2-a]pyridine; and 3-hydroxymethyl-2-methyl-8-(2-pyridyl-methoxy)imidazo[1,2-a]pyridine.

EXAMPLE 6

3-Cyanomethyl-2-methyl-8-(phenylpropoxy)-imidazo[1,2-a]pyridine

A mixture of 5.3 g of 2-amino-3-(3-phenylpropoxy)-pyridine, 3.2 g of 3-chloro-4-oxopentanonitrile, 2.0 g sodium bicarbonate, and 50 ml dimethoxyethane was heated at reflux for 24 hrs., then stirred at room temperature 66 hrs. the solvent was removed in vacuo, the brown residue was taken up in 100 ml methylene chloride, filtered, dried over potassium carbonate and evaporated in vacuo to leave a brown gum residue. The residue was chromatographed on silica gel using first chloroform, then switching to 1:1 chloroform/ethyl acetate. The early eluates were combined and evaporated and the resultant residue crystallized from isopropyl/ether to give the title compound (m.p. 143°–145° C.).

In similar manner, reaction of 2-amino-3-(2-phenylethyl)pyridine (which is prepared by amination of 3-(2-phenyl ethyl)-pyridine with sodium amide in ammonia and N,N-dimethylaniline) with 3-chloro-4-oxo-pentanonitrile in ethanol in the presence of triethylamine gives 3-cyano-methyl-2-methyl-8-(2-phenylethyl-)imidazo[1,2-a]pyridine.

EXAMPLE 7

8-Benzyloxy-2-hydroxymethylimidazo[1,2-a]pyridine

To an ice-cooled suspension of 1.5 g lithium aluminium hydride in 150 ml tetrahydrofuran there was added 15.0 g 8-benzyloxyimidazo[1,2-a]pyridine-2-carboxylic acid ethyl ester (obtained according to Example 5) in portions so that the temperature remains below 10° C. After stirring at 0°–5° C. for an additional 1 hr., 1.5 ml water was added dropwise at 0°–10° C., followed by 1.5 ml 15% aqueous sodium hyroxide and then 4.5 ml water. The mixture was allowed to warm to room temperature with stirring, and was then suction-filtered in a sintered glass funnel. The solids left in the funnel were thoroughly washed with 4×200 ml hot chloroform.

The filtrate and washings were combined and evaporated in vacuo to give the title compound (m.p. 138°–140° C.).

In a similar manner, reduction of the esters obtained according to Example II leads to the following compounds:

8-(4-fluorobenzyloxy)-2-hyroxymethylimidazo[1,2-a]pyridine, 8-(3,4-dichlorobenzyloxy)-2-hydroxymethylimidazo[1,2-a]pyridine, 8-(2-fluorobenzyloxy)-2-hydroxymethylimidazo[1,2-a]pyridine.

EXAMPLE 8

8-Benzyloxy-2-hydroxymethyl-3-methylimidazo[1,2-a]pyridine

To an ice-cooled suspension of LiAlH$_4$(1.03 g) in tetrahydrofuran (THF) (200 ml) there was added 8-benzyloxy-2-methoxycarbonyl-3-methyl-imidazo[1,2-a]pyridine (13.3 g) obtained according to Example VI in several portions over 20 minutes. The temperature was maintained below +8° C. After all the substance had been added, stirring with cooling was continued for 30 min. and thereafter the mixture was stirred at room temperature for another hour. The reaction mixture was cooled to 3° C. and to the stirred mixture there was first added 1.09 ml of water, then 1.63 ml of 10% aqueous NaOH and finally 3.27 ml water. The resulting mixture was stirred for 5 min. on the ice bath and 5 min. at room temperature and then filtered. The solid was washed with 2×100 ml of hot THF and the wash fluid was added to the original filtrate. The solution was stripped to yield a brown powder which was triturated for 1 hr. in 150 ml CHCl$_3$. After filtration and washing a slightly impure product was obtained (m.p. 172°–175° C.).

EXAMPLE 9

8-Benzyloxy-2-chloromethylimidazo[1,2-a]pyridine

The product of Example 7 (9.35 g) was suspended in 50 ml CHCl$_3$. The stirred suspension was cooled and a solution of thionylchloride (8.3 g) in 5 ml CHCl$_3$ was added over a period of 5 min. so as to keep the temperature below 20° C. A light grey slurry was obtained which was quenched by pouring it into a mixture of aqueous NaHCO$_3$ (25 ml of 1.1 M), ice and CHCl$_3$. Water, aqueous NaCHO$_3$ and CHCl$_3$ was added and the resulting mixture having 450 ml organic phase and 500 ml aqueous phase was stirred until all solids was dissolved. The phases were separated and the aqueous phase extracted with CHCl$_3$. The combined organic phases were washed with brine (2×300 ml), driev over Na$_2$SO$_4$ and stripped to give a residue which was trituated in 100 ml of ether. Filtration and washing of the solid gave the desired product (m.p. 163° C.).

EXAMPLE 10

8-Benzyloxy-3-dimethylaminomethyl-2-methylimidazo[1,2-a]pyridine

Into a one liter flask there was placed 8-benzyloxy-2-methylimidazo[1,2-a]pyridine (114 g) (from Example IB), dimethylamine hydrochloride (41.6 g) paraformaldehyde (15.23 g) and methanol (450 ml) and the mixture was refluxed with stirring for 1.5 hours. Thereafter the mixture was boiled, open to the air, for ¾ hrs. After cooling to room temperature and treatment with concentrated hydrochloric acid (45 ml) the mixture was stirred for 18 hrs., filtered and the thick white solid mass formed was washed with methanol and 200 ml of anhydrous ether and dried. (M.p. of the hydrochloride salt of the desired compound: 210°–211° C.). By reacting the appropriate imidazo[1,2-a]pyridine compounds with dimethylamine hydrochloride and paraformaldehyde in a manner similar to the one described above, the following compounds are obtained:

3-dimethylaminomethyl-8-(4-fluorobenzyloxy)-2-methylimidazo[1,2-a]pyridine,
8-(3,4-dichlorobenzyloxy)-3-dimethylaminomethyl-2-methylimidazo[1,2-a]pyridine,
3-dimethylaminomethyl-2-methyl-8-(2-phenylethoxy)imidazo[1,2-a]pyridine,
8-benzyloxy-3-dimethylaminomethyl-imidazo[1,2-a]pyridine and the corresponding 2-hydroxymethyl analogues thereof (e.g. 8-benzyloxy-3-dimethylaminomethyl-2-hydroxymethylimidazo[1,2-a]pyridine.

EXAMPLE 11

8-Benzyloxy-3-cyanomethyl-2-methylimidazo[1,2-a]pyridine

STEP A: Preparation of 8-benzyloxy-3-dimethylaminomethyl-2-methyl-imidazo[1,2-a]pyridine methiodide.

8-Benzyloxy-3-dimethylaminomethyl-2-methylimidazo[1,2-a]pyridine hydrochloride (1.325 kg) from Example 10 was dissolved in 4.5 liters of hot water. The solution was made strongly basic with 50% NaOH-solution. The chilled mixture was extracted with dichloromethane (3×1.5 liters) and the combined extracts were washed with brine (1.5 liters). The dichloromethane extract was concentrated on a rotary evaporator. The residual oil was dissolved in 2.5 liters of ethanol. With stirring the solution was cooled and methyl iodide (232 ml) was added dropwise over a period of 1.5 hrs. The mixture was allowed to warm to room temperature overnight under continued stirring. The white precipitate was collected after about 18 hrs. of stirring, washed with 1.5 liters of ethanol and 3 liters of ether. The resulting product is ready for use in Step B below.

By reacting the 3-dimethylaminomethyl-imidazo[1,2-a]pyridines obtained in Example XII with methyliodide according to the process described above, the following quaternary salts are obtained:

3-dimethylaminomethyl-8-(4-fluorobenzyloxy)-2-methylimidazo[1,2-a]pyridine methiodide,
8-(3,4-dichlorobenzyloxy)-3-dimethylaminomethyl-2-methylimidazo[1,2-a]pyridine methiodide,
3-dimethylaminomethyl-2-methyl-8-(2-phenylethoxy)imidazo[1,2-a]pyridine methiodide,
8-benzyloxy-3-dimethylaminomethyl-imidazo[1,2-a]pyridine methiodide and
8-benzyloxy-3-dimethylaminomethyl-2-hydroxymethyl-imidazo[1,2-a]pyridine methiodide.

STEP B: Preparation of title compound.

A mixture of the methiodide of Step A (1.552 kg) and sodium cyanide (310 g) in 8.4 liters of dimethylformamide was stirred and heated at a steam bath for 1 hr. The dark brown reaction mixture was poured into 30 liters of ice water and the mixture was stirred for 1 hr. The brown solid product was collected, washed with cold water and allowed to air dry. This material was dissolved in 3.8 liters of hot methanol and treated with hydrogen chloride gas until strongly acidic. The mixture was cooled and the product collected. After washing with methanol, acetonitrile and finally with ether the title product as a hydrochloride salt was obtained.

The salt was resuspended in water and made strongly alkaline with 10% sodium hydroxide. The product was extracted with dichloromethane (3×2.5 liters) and the combined extracts concentrated on a rotary evaporator. The residue was dissolved in 3.6 liters of hot acetonitrile, and the resulting solution filtered through a glass wool plug and the filtrate was refrigerated overnight. The desired product was then washed with cold acetonitrile (m.p. 163°–166° C.).

Using this procedure with the quaternary salts listed above under Example 11A, thereby applying an appropriate solvent such as dimethylformamide, dimethylsulfoxide, ethanol etc., the following compounds are obtained:

3-cyanomethyl-8-(4-fluorobenzyloxy)-2-methylimidazo[1,2-a]pyridine;
3-cyanomethyl-8-(3,4-dichlorobenzyloxy)-2-methylimidazo[1,2-a]pyridine;
3-cyanomethyl-2-methyl-8-(2-phenylethoxy)imidazo[1,2-a]pyridine;
8-benzyloxy-3-cyanomethylimidazo[1,2-a]pyridine; and
8-benzyloxy-3-cyanomethyl-2-hydroxymethyl-imidazo[1,2-a]pyridine.

EXAMPLE 12

3-Chloromethyl-8-(2-fluorobenzyloxy)-2-methylimidazo[1,2-a]pyridine

A mixture of 8-(2-fluorobenzyloxy)3-hydroxymethyl-2-methyl-imidazo[1,2-a]pyridine from Example 5 (1 g) and phosphorylchloride (15 ml) was heated under reflux for 1 hr. Excess phosphorylchloride was distilled off in vacuo, the residue dissolved in hot ethanolic HCL and the mixture filtered to give the title compound as the hydrochloride salt.

By subjecting other 3-hydroxymethyl-imidazo[1,2-a]pyridines obtained according to Example 5 to substantially the same reaction as described above, the hydrochloride salts of the following 3-chloromethyl-compounds are obtained:

8-(4-chlorobenzyloxy)-3-chloromethyl-2-methyl-imidazo[1,2-a]pyridine,
3-chloromethyl-8-(4-fluorobenzyloxy)-2-methyl-imidazo[1,2-a]pyridine,
3-chloromethyl-2-methyl-8-(2-phenylethoxy)-imidazo[1,2-a]pyridine,
8-benzyloxy-3-chloromethyl-2-methyl-imidazo[1,2-a]pyridine, and
3-chloromethyl-2-methyl-8-(2-pyridyl-methoxy)-imidazo[1,2-a]pyridine.

EXAMPLE 13

3-Cyanomethyl-8-(2-fluorobenzyloxy)-2-methylimidazo[1,2-a]pyridine

A mixture of 3-chloromethyl-8-(2-fluorobenzyloxy)-2-methyl-imidazo[1,2-a]pyridine hydrochloride from Example 12 (1.3 g), potassium cyanide (1.6 g) and dimethylsulfoxide (20 ml) was stirred at room temperature for 16 hrs.

The mixture was poured into 200 ml cold water and extracted with 2×150 ml dichloromethane, the combined organic extracts were dried over potassium carbonate, the mixture filtered, and the filtrade exaporated in vacuo. The liquid residue was chromatographed on silica gel (30 g) eluting with ethyl acetate-dichloromethane, the fractions containing the product were evaporated in vacuo, and the residue was crystallized from acetonitrile to give the desired compound (m.p. 172°–173° C.) In a similar manner, using the various 3-chloromethyl-imidazo[1,2-a]pyridines obtained in Example 12 the following 3-cyanomethyl-compounds are prepared:
8-(4-chlorobenzyloxy)-3-cyanomethyl-2-methylimidazo[1,2-a]pyridine,
3-cyanomethyl-8-(4-fluorobenzyloxy)-2-methylimidazo-[1,2-a]pyridine,
3-cyanomethyl-2-methyl-8-(2-phenylethoxy)imidazo[1,2-a]pyridine, and
3-cyanomethyl-2-methyl-8-(2-pyridyl-methoxy)imidazo[1,2-a]pyridine.

EXAMPLE 14

8-Benzyloxy-2-chloromethylimidazo[1,2-a]pyridine

A mixture of 8-benzyloxy-2-hydroxymethylimidazo[1,2-a]pyridine (2 g) and phosphorylchloride (10 ml) was heated on a steam bath for 1 hr. Excess phosphoryl chloride was distilled off in vacuo, the solid residue triturated with acetonitrile and the mixture filtered to give the title product as the hydrochloride salt.

In substantially the same manner, using 2-hydroxymethyl-compounds obtained according to the procedure of Examples 7 and 8 the following 2-chloromethyl-imidazo[1,2-a]pyridine compounds are obtained as the hydrochloride salts:
2-chloromethyl-8-(4-methoxybenzyloxy)-imidazo[1,2-a]pyridine,
2-chloromethyl-8-(4-fluorobenzyloxy)-imidazo[1,2-a]pyridine
2-chloromethyl-8-(3,4-dichlorobenzyloxy)-imidazo[1,2-a]pyridine,
2-chlorormethyl-8-(2-fluorobenzyloxy)-imidazo[1,2-a]pyridine,
8-benzyloxy-2-chloromethyl-3-methylimidazo[1,2-a]pyridine.

EXAMPLE 15

8-Benzyloxy-2-cyanomethyl-imidazo[1,2-a]pyridine

A mixture of 1.79 g 8-benzyloxy-2-chloromethylimidazo[1,2-a]pyridine, 0.90 g sodium cyanide, and 15 ml dimethylformamide was heated on a steam bath for 1.5 hr. The mixture was cooled and evaporated in vacuo, the residue was taken up in chloroform (50 ml) and filtered through a pad of silica gel, the filtrate was evaporated in vacuo, and the residue recrystallized from acetonitrile to give the title compound (m.p. 148°–150° C.).

In a similar manner, reaction of the appropriate chloromethylimidazo[1,2-a]pyridine from Example 14 with an alkali metal cyanide in a suitable solvent leads to the following compounds:
2-cyanomethyl-8-(4-fluorobenzyloxy)imidazo[1,2-a]pyridine,
2-cyanomethyl-8-(3,4-dichlorobenzyloxy)imidazo[1,2-a]pyridine,
2-cyanomethyl-8-(2-fluorobenzyloxy)imidazo[1,2-a]pyridine.

EXAMPLE 16

8-Benzyloxy-3-(2-hydroxyethyl)-2-methylimidazo[1,2-a]pyridine

A solution of 26 g of 8-benzyloxy-3-cyanomethyl-2-methyl-imidazo[1,2-a]pyridine, 50 ml of 15% sodium hydroxide solution 100 ml of water, and 100 ml of ethanol was heated at reflux for 6 hrs. The reaction mixture was distilled until 100 ml of distillate had been collected. The aqueous portion was washed twice with dichloromethane and then treated with a 6 N hydrochloric acid to pH 6. Filtration afforded 8-benzyloxy-2-methyl-imidazo[1,2-a]pyridine-3-acetic acid. 2.0 g of this acid was added to 1 g of lithium aluminium hydride in 100 ml of tetrahydrofuran and was stirred for 5 hrs. at room temperature. The reaction mixture was treated with 1 ml of water, 1 ml of 15% sodium hydroxide solution, then with 3 ml of water. Filtration of salts and evaporation of the filtrate gave the title product after recrystallization from acetonitrile (m.p. 134°–138° C.).

EXAMPLE 17

3-Cyanomethyl-2-methyl-8-(2-thienylmethoxy)imidazo[1,2-a]pyridine

A mixture of 2-amino-3-(2-thienylmethoxy)pyridine (5.35 g), 3-chloro-4-oxopentanontrile (4.5 g) and triethylamine was stirred together in ethanol and heated under reflux for 27 hours. The solvent was evaporated in vacuo and the residue was partitioned between $CH_2Cl_2$ (100 ml) and 15% $K_2CO_3$ (30 ml). The organic layer was separated, washed with 15% $K_2CO_3$ (2×30 ml) and dried ($Na_2SO_4$). The solvent was evaporated in vacuo and the residue was recrystallized from acetonitrile to yield the title compound (m.p. 155°–157° C.).

EXAMPLE 18

8-Benzyloxy-3-cyanomethyl-2-methyl-imidazo[1,2-a]pyridine 3-cyanomethyl-8-hydroxy-2-methyl-imidazo[1,2-a]pyridine (1.0 g) was dissolved in DMF (25 ml) and sodium hydride (0.26 g, 50% in oil) was added. The mixture was stirred at room temperature for 30 minutes and then benzyl chloride (0.7 g) was added and stirring while heating to to 60° C. was continued for 3 hrs. The solvent was evaporated in vacuo, the residue partitioned between chloroform and water, the organic layer separated, dried ($MgSO_4$) and evaporated in vacuo. The residue was recrystallized from acetonitrile to give the title compound (m.p. 163°–166° C.).

EXAMPLE 19

8-Benzyloxy-3-cyanomethyl-2-methyl-imidazo[1,2-a]pyridine

A suspension of 8-benzyloxy-2-methyl-imidazo[1,2-a]pyridine-3-acetamide (3 g) in dioxane was cooled to 5°–10° C. To the suspension there was added over a period of 5 minutes a solution of trifluoroacetic anhydride (6 g) in dioxane. The mixture was maintained cool and stirred for 30 minutes. Thereafter the mixture was allowed to warm to room temperature and was stirred for a further four hours. The mixture was then diluted with ice water and the precipitate was filtered. After recrystallization from ethylacetate the desired compound was obtained (m.p. 163°–166° C.).

EXAMPLE 20

8-Benzyloxy-2-methyl-5,6,7,8-tetrahydroimidazo[1,2-a]pyridine

STEP A: Preparation of 8-hydroxy-2-methyl-5,6,7,8-tetrahydroimidazo[1,2-a]pyridine hydrochloride.

A mixture of 8-benzyloxy-2-methyl-imidazo[1,2-a]pyridine (5.9 g), 6.1 N HCl (4.2 ml), 10% Palladium-on-charcoal (5.9 g) and 240 ml ethanol was hydrogenated under a H$_2$-pressure of about 3.5 kg/cm$^2$ for 22 hrs. at room temperature, after which period a further 2 g of fresh catalyst was added and hydrogenation continued for another 45 hrs. After filtration and evaporation of the solvent at the reduced pressure, the title compound is obtained as a pale yellow solid with m.p. 140°–152° C.

STEP B: Preparation of 8-benzyloxy-2-methyl-5,6,7,8-tetrahydroimidazo[1,2-a]pyridine.

The compound of Step A (3.49 g) was suspended in N,N-dimethylformamide (25 ml) and potassium t-butoxide (2.18 g) was added. The mixture was stirred 5 min. at ice bath temperatures and 10 min. at room temperature and thereafter the mixture was cooled to ice bath temperature again.

This reaction mixture (which contains the free base of the compound of Step A) was added stepwise to an ice cooled, stirred suspension of 1.02 g of 50% dispersion of sodium hydride. The resulting mixture is stirred 30 min. on an ice-water bath. To this cold suspension (which contains the alkoxide of the compound of Step A) there was added a solution of benzyl chloride (2.48 g) in DMF. The resultant mixture was stirred in an ice bath for 5 min., at room temperature for 5 min., and then in a heating bath at 85°–90° C. for 1.5 hrs. The solvent was evaporated off at reduced pressure. To the residue there was added water and the mixture was extracted three times with a 1:1 mixture of methylenechloride and ether. The combined extracts were washed with brine, dried over Na$_2$SO$_4$ and the solvent evaporated at reduced pressure. The oily residue was chromatographed on silica gel, using a 1:1 mixture of acetone and methylene chloride as eluant. The title compound was obtained as a yellow oil with the following PMR spectrum (DMSO-d$_6$): 2.08(3H,s); 1.7–2.2(4H,m); 3.65–4.1(2H,m); 4.42(1H, deformed triplet); 4.70(2H,s); 6.73(1H,s); 7.30(5H,s).

EXAMPLE 21

8-Benzyloxy-3-dimethylaminoethyl-2-methyl-5,6,7,8-tetrahydroimidazo[1,2-a]pyridine A mixture consisting of the product of Example 20 (1.52 g), dimethylamine hydrochloride (565 mg), paraformaldehyde (238 mg) and ethanol (10 ml) was refluxed for four hrs. After cooling to room temperature, the solvent was evaporated under reduced pressure. The residue was dissolved in chloroform, the solution washed four times with 5% aqueous potassium carbonate, dried over Na$_2$SO$_4$ and then the solvent was evaporated on a rotary evaporator. The residue was chromatographed on silica gel, eluting with acetone, to obtain the title compound (m.p. 68°–70° C.).

EXAMPLE 22

8-Benzyloxy-3-cyanomethyl-2-methyl-5,6,7,8-tetrahydroimidazo[1,2-a]pyridine

STEP A: Preparation of 8-benzyloxy-3-dimethylaminomethyl-2-methyl-5,6,7,8-tetrahydroimidazo[1,2-a]pyridine methiodide.

To a solution of 8-benzyloxy-3-dimethylaminomethyl-2-methyl-5,6,7,8-tetrahydroimidazo[1,2-a]pyridine (2.56 g) in acetone (35 ml) there was added a solution of methyl iodide (1.22 g) in acetone (2 ml). The resulting solution was stirred for 16 hrs. at room temperature. The solvent was then evaporated on a rotary evaporate and the last traces (of solvent) were removed under the high vacuum. The obtained title compound was hygroscopic powder with a very broad melting range having the following PMR spectrum (DMSO-d$_6$): 2.0(4H,m); 2.25(3H,s); 3.05(9H,s); 3.8–4.2(2H,m); 4.55(2H, broad singlet) (3-CH$_2$-N and H$_8$); 4.75(2H,s); 7.30(5H, broad singlet).

STEP B: Preparation of title compound.

The compound of Step A (3.3 g) and potassium cyanide (1.22 g) were added to dimethylformamide (30 ml) and the mixture was stirred at 90° C. for 90 min. The solvent was removed under reduced pressure and the residue was dissolved in a mixture of chloroform and water. The layers were separated and the aqueous phase was extracted three times with chloroform. The chloroform fractions were combined, washed with brine, dried over Na$_2$SO$_4$ and evaporated on a rotary evaporator. The residue was chromatographed on silica gel, eluting with a 1:1 mixture of acetone and methylene chloride, and the title compound is obtained (m.p. 131.5°–134.5° C.).

EXAMPLE 23

3-Cyanomethyl-2-methyl-8-phenoxyimidazo[1,2-a]pyridine

A mixture of 8-hydroxy-2-methylimidazo[1,2-a]pyridine (14.8 g), bromobenzene (15.7 g), copper powder (1.0 g) and powdered potassium hydroxide (5.6 g) in N-methyl pyrrolidone was heated under reflux for 4 hrs. The solvent was removed by distillation and the residue suspended in dichloromethane, washed with 10% sodium hydroxide solution and the dichloromethane was evaporated to give 2-methyl-8-phenoxyimidazo[1,2-a]pyridine. Treatment of this compound in accordance with Examples 10 and 11 yields the desired product.

EXAMPLE 24

5-Phenylmethoxy-2,3-dimethylimidazo[1,2-a]pyridine

Sodium hydride (50% in oil, 4.8 g) is added to a solution of benzyl alcohol (6.48 g) in dimethylformamide (200 ml). 5-chloro-2,3-dimethylimidazo[1,2-a]pyridine hydrobromide (10.5 g) is added and the mixture is stirred at room temperature for two hours.

The solvent is removed in vacuo and the residue is partitioned between water (500 ml) and ether (400 ml). The ether layer is separated, dried over anhydrous sodium sulfate and concentrated in vacuo to yield a yellow oil which is chromatographed on silica gel (300 g) using ether as an eluant. After an initial forerum of a yellow oil, the product is obtained which crystallized from 1-chlorobutane-hexane mixture.

Similarly, the use of benzylamine in place of benzyl alcohol gives 5-benzylamino-2,3-dimethylimidazo[1,2-a]pyridine.

EXAMPLE 25

6-Benzylamino-2-methylimidazo[1,2-a]pyridine-3-acetonitrile

A mixture of 2-amino-5-benzylamino pyridine (4.0 g), triethylamine (2.1 g), 3-chloro-4-oxopentanenitrile (2.7 g) and acetonitrile (50 ml) is stirred and heated under reflux for 18 hr. The solvent is removed in vacuo, and the residue is dissolved in chloroform (200 ml). The solution is washed with water (4×100 ml), dried over anhydrous potassium carbonate and the chloroform is removed in vacuo. The residue is chromatographed on silica gel (200 g) using chloroform as the eluant. The product is obtained and crystallized from acetonitrile.

Similarly the use of 2-amino-5-phenylmethoxy pyridine gives 6-phenylmethoxy-2-methylimidazo[1,2-a]pyridinyl-3-acetonitrile.

EXAMPLE 26

7-Phenylmethoxy-2-methylimidazo[1,2-a]pyridine-3-acetonitrile

A solution of 2-amino-4-phenylmethoxypyridine (1.45 g), triethylamine (0.73 g) and 3-chloro-4-oxopentanenitrile (0.95 g) in methanol (40 ml) is heated under reflux for three hours. After one hour, additional 3-chloro-4-oxopentanenitrile (0.5 g) and triethylamine (0.36 g) is added. The solvent is removed in vacuo, and the residue is partitioned between methylene chloride (50 ml) and 2% sodium hydroxide (50 ml). The methylene chloride layer is removed and concentrated in vacuo to give 1.5 g of crude product.

A solution of crude product (1.1 g) and 0.6 ml pyridine in 20 ml p-dioxane is cooled in an ice-bath and treated with 0.6 ml trifluoroacetic anhydride in 2 ml p-dioxane. After removal of the ice bath, the reaction is stirred for one hour, diluted with water (300 ml) and treated with saturated sodium bicarbonate to pH 7–8. Filtration gives 0.8 g of a solid which is chromatographed on silica gel (125 g) using 3% methanol in methylene chloride to give the product which crystallizes from ethyl acetate.

Similarly, the use of 2-amino-4-benzylaminopyridine in the above procedures yields 7-benzylamino-2-methylimidazo[1,2-a]pyridine-3-acetonitrile.

EXAMPLE 27

8-Allyloxy-3-cyanomethyl-2-methylimidazo[1,2-a]pyridine

A. 8-Benzyloxy-3-cyanomethyl-2-methylimidazo[1,2-a]pyridine (40 g, 0.14 mol), 1,4-cyclohexadiene (50 g, 0.62 mol), dimethylformamide (600 ml) and palladium black (2 g) are stirred together and heated. At 45° C., a sudden exotherm occurs and the temperature rises rapidly to 75°–80°. Heating is discontinued and the mixture stirred for 1 hr. The catalyst is removed by filtration and the cyclohexadiene removed in vacuo. The dimethylformamide is removed in vacuo (0.1 mm) at 55° to afford 3-cyanomethyl-2-methyl-8-hydroxy imidazo[1,2-a]pyridine (27 g, 0.14 mol).

B. 3-cyanomethyl-2-methyl-8-hydroxyimidazo[1,2-a]pyridine (60.5 g, 0.32 mol) and dry dimethylformamide (1600 ml) are stirred together and sodium hydride (15.4 g, 0.32 mol, 50% in oil) added during 15 minutes. The mixture is stirred 1.5 hr after the addition of sodium hydride. Allyl bromide (38.7 g., 0.32 mol) is added dropwise during 1 hr. After the addition of allyl bromide, the reaction is stirred for an addition 1 hr. The dimethylformamide is removed in vacuo. The residue partitioned between water (1 L) and chloroform (3 L), the organic layer separated, washed with water (1 L) dried over anhydrous magnesium sulfate and the solved removed in vacuo. Residual dimethylformamide is removed in vacuo (0.1 mm). The residual oil is dissolved in chloroform (300 ml) and filtered through a silica gel plug (100 g, tlc grade 60H) to remove colored materials. This process yields 29.2 g of an oil.

C. Treatment of the oil produced in Step B with ethereal hydrogen chloride gives 8-allyloxy-3-cyanomethyl-2-methylimidazo[1,2-a]pyridine HCl (29.9 g, 0.11 mol.) mp 177°–179° C.

EXAMPLE 28

3-Cyanomethyl-2-methyl-8-(2-phenylethyl)imidazo[1,2-a]pyridine

A. Sodium amide is prepared from sodium (16 g, 0.69 mol) and 250 ml liquid ammonia in the presence of ferric trinitrate nonahydrate (0.16 g). N,N-Dimethylaniline (100 ml) is added and the mixture stirred without cooling. An additional 77 ml N,N-dimethylaniline is added and the mixture warmed to room temperature. 3-(2-Phenylethyl)pyridine (85 g, 0.46 mol) is added dropwise and the mixture heated at 160°–167° C. for 5 hr. Upon cooling to room temperature, 5% sodium hydroxide (75 ml), water (300 ml) and hexanes (150 ml) are added. The mixture is stirred for 15 minutes and filtered to give 40 g of a yellow solid. Fractional crystallization from isopropyl ether, followed by subsequent crystallizations from ethyl acetate gives (24.6 g, 0.12 mol) 2-amino-3-(2-phenylethyl)pyridine, mp 106°–108° C.

B. 2-Amino-3-(2-phenylethyl)pyridine (20.9 g, 0.11 mol), triethylamine (15.2 g, 0.15 mol) and 3-chloro-4-oxopentanenitrile (7 g, 0.053 mol) in 250 ml ethanol are heated under reflux for 1.25 hr. An addition (7 g, 0.053 mol) 3-chloro-4-oxopentanenitrile is added and heating continued for 2.5 hr. The solvent is removed in vacuo and the residue treated with water (300 ml) and acidified with 6 N hydrochloric acid. The acidic aqueous layer is extracted with ethyl acetate and the ethyl acetate extracts combined and washed with water. The water washes are combined with the acidic aqueous layer and neutralized by the addition of 25% sodium hydroxide. The basic aqueous layer is extracted with dichloromethane and the extracts combined and dried over anhydrous magnesium sulfate. Following filtration, the dichloromethane is removed uner reduced pressure to afford 10 g of a solid. Recrystallization from acetonitrile gives (6.5 g, 0.024 mol), 3-cyanomethyl-2-methyl-8-(2-phenylethyl)imidazo[1,2-a]pyridine, mp 120°–123° C.

C. By treating 2-amino-5-(2-phenylethyl)pyridine in a manner similar to that described in above Example 28 B, there is obtained 3-cyanomethyl-2-methyl-6-(2-phenylethyl)imidazo[1,2-a]pyridine, mp 139°–141° C.

EXAMPLE 29

3-Cyanomethyl-2-methyl-8-(3-phenylpropyl)imidazo[1,2-a]pyridine

A. 2-Methyl-8-Formylimidazo[1,2-a]pyridine

A mixture of 2-aminonicotinaldehyde (92.8 g, 0.76 mol) and bromoacetone (114.5 g, 0.84 mol) in dimethoxyethane (980 ml) is stirred for 2 hr. at room temperature and then heated at 65° with stirring for 14 hr. The solid which separates is isolated by filtration, dissolved in 800 ml absolute ethanol and heated under reflux for 6 hrs. The ethanol solvent is removed under reduced pressure and the residue treated with 138 ml 6 N hydrochloric acid in 750 ml water for 0.5 hr. The acidic aqueous layer is washed with ether (2×300 ml) and basified with cooling (78 ml 50% sodium hydroxide and 25 g sodium bicarbonate). The aqueous layer is extracted with dichloromethane. The extracts are combined and dried over anhydrous sodium sulfate. Following filtration, the solvent is removed under reduced pressure to afford 2-methyl-8-formylimidazo[1,2-a]pyridine, mp 136°–139.5° C.

B. 2-Methyl-8-(1-hydroxy-3-phenylpropyl)imidazo[1,2-a]pyridine

Phenylethyl magnesium bromide, prepared from 2-phenylethyl bromide (64.8 g, 0.35 mol) and magnesium (8.2 g, 0.34 mol) in 165 ml anhydrous ether, is added to 2-methyl-8-formylimidazo[1,2-a]pyridine (40.0 g, 0.25 mol) in 750 ml dry tetrahydrofuran.

After stirring for 18 hr. at room temperature, 50 ml saturated ammonium chloride is added while maintaining the temperature between 6°–8°. An additional 250 ml water is added and the organic layer separated. Removal of the solvent under reduced pressure gives a residue which is treated with water (250 ml), ether (150 ml) and 42 ml 6 N hydrochloric acid. The acidic aqueous layer is separated, washed with ether and basified with 15% sodium hydroxide. The basic aqueous layer is extracted with ether; the extracts combined and dried over anhydrous sodium sulfate. Following filtration, the solvent is removed under reduced pressure to afford 2-methyl-8-(1-hydroxy-3-phenylpropyl)imidazo[1,2-a]pyridine.

C. 2-Methyl-8-(1-chloro-3-phenylpropyl)imidazo[1,2-a]pyridine

To a dichloromethane solution (980 ml) of 2-methyl-8-(1-hydroxy-3-phenylpropyl)imidazo[1,2-a]pyridine (45.6 g, 0.17 mol) at −24° to −27° C. is added a dichloromethane solution (200 ml) of thionyl chloride (21.1 g, 0.19 mol) over 0.5 hr. with stirring.

The mixture is stirred for an additional 1 hr. and poured onto ice. The acidic aqueous solution is basified to pH 8 using 6 N sodium hydroxide and solid sodium bicarbonate. The basic aqueous layer is extracted with dichloromethane, then the extracts are combined and dried over anhydrous magnesium sulfate. Following filtration, the solvent is removed under reduced pressure to afford 2-methyl-8-(1-chloro-3-phenylpropyl)imidazo[1,2-a]pyridine.

D. 2-Methyl-8-(3-phenylpropyl)imidazo[1,2-a]pyridine

To a stirred suspension of LAH (3.95 g, 0.10 mol) in 250 ml tetrahydrofuran at 28°–31° under a nitrogen atmosphere is added dropwise a tetrahydrofuran solution (75 ml) of 2-methyl-8-(1-chloro-3-phenylpropyl)imidazo[1,2-a]pyridine (18.0 g, 0.063 mol). The suspension is heated under reflux for 16.5 hr., cooled to 0° and to it added with caution water (4 ml) followed by 15% sodium hydroxide (4 ml) and water (12 ml). The suspension is stirred with Celite, filtered and the filter cake washed repeatedly with dichloromethane.

The dichloromethane filtrates are combined and dried over anhydrous sodium sulfate. Following filtration, the solvent is removed under reduced pressure to afford 2-methyl-8-(3-phenylpropyl)imidazo[1,2-a]pyridine.

E. 3-Cyanomethyl-2-Methyl-8-(3-phenylpropyl)imidazo[1,2-a]pyridine

In a manner similar to that described in Examples 10 and 11, reaction of 2-methyl-8-(3-phenylpropyl)imidazo[1,2-a]pyridine with dimethylamine and formaldedyde followed by treatment of the 3-dimethylaminomethyl derivative thereby formed with methyl iodide and thence reaction of the resulting 3-dimethylaminomethyl methiodide salt with sodium cyanide yields 3-cyanomethyl-2-methyl-8-(3-phenylpropyl)imidazo[1,2-a]pyridine, m.p. 66.5°–68° C.

F. 3-Cyanomethyl-2-Methyl-6-(3-Phenylpropyl)imidazo[1,2-a]pyridine

By utilizing 5-aminonicotinaldehyde as the starting compound in above Example 29-A and going through the sequence of reactions described in Steps A through E hereinabove there is obtained 3-cyanomethyl-6-(3-phenylpropyl)imidazo[1,2-a]pyridine.

EXAMPLE 30

2-Methyl-3-Nitroso-8-(Phenylmethoxy)imidazo[1,2-a]pyridine

To a stirred mixture of 10.0 g (42.2 mmol) of 2-methyl-8-(phenylmethoxy)imidazo[1,2-a]pyridine, 150 ml of water and 150 ml of chloroform is added cautiously (EXOTHERM) 179.5 ml (2.15 moles) of concentrated hydrochloric acid and the resultant mixture is heated to an internal temperature of approximately 55° C. To this stirred and heated mixture is added at a rate of approximately 7 ml/minute a solution of of 151 g (2.11 moles) sodium nitrite (97%) in 660 ml of water to produce a vigorous, but manageable, reflux. When the addition is complete, the reaction mixture is allowed to cool to room temperature. The lower (CHCl$_3$) layer is drawn off and the aqueous layer extracted with three—150 ml portions of chloroform. The combined chloroform extracts are washed with two—450 ml volumes of 2.4 M sodium carbonate solution, then with a single 500 ml portion of saturated aqueous sodium chloride. The extracts are concentrated in vacuo (rotary evaporator, 45°) to less than one-half the original volume, dried over anhydrous sodium sulfate and evaporated to a viscous oil. Chromatography of the oil on silica gel, eluting with chloroform/ethyl acetate (1/1) yields the title compound as a crystalline solid, mp 147.5°–149.5° C. (dec).

EXAMPLE 31

3-Amino-2-methyl-8-(phenylmethoxy)imidazo[1,2-a]pyridine phosphate

A. To a stirred mixture of 3.2 g (12 mmol) of 2-methyl-3-nitroso-8-(phenylmethoxy)imidazo[1,2-a]pyridine in 24 ml of glacial acetic acid and 33.5 ml of water is added portionwise 3.23 g (49.5 mmol) of zinc powder over a two hour period. When addition is complete, the reaction mixture is stirred at room temperature for 30 minutes. The mixture is filtered through Celite, and the filtrate diluted with 75 ml each of ether and methylene chloride and washed with a solution of 250 ml of 1.7 M sodium hydroxide. The resultant emulsion is filtered through Celite and the Celite pad washed thoroughly with 250 ml of hot chloroform.

The layers of the filtrate are separated and the aqueous phase extracted with the chloroform used to wash the Celite pad. The combined organic extracts are washed with two-125 ml portions of water and one-150 ml volume of saturated aqueous sodium chloride concentrated under reduced pressure to a volume of approximately 100 ml. The concentrate is dried over anhydrous sodium sulfate and the solvent removed under reduced pressure (rotary evaporator, 40° C.) to give a slightly tacky brown powder that is triturated in ether (75 ml)—methylene chloride (1 ml) to yield the free base of the title compound as a light brown powder, mp 126°–131.5° (dec).

B. 850 mg (3.37 mmol) of the free base is dissolved in approximately 40 ml of dry acetonitrile. To the stirred solution is added 8 ml of an acetonitrile solution containing 3.4 mmol of phosphoric acid. A precipitate forms and the mixture is diluted with 70 ml of ether and filtered. The solid is triturated in 60 ml of fresh ether and filtered to give the curde phosphate salt which upon recrystallization from methanol-ethyl acetate yields the title phosphate salt containing 1.3 moles of water of crystallization, mp 214°–214.5° C. (dec).

EXAMPLE 32

3-Cyanomethyl-2-methyl-7-(2-phenylethyl)-imidazo[1,2-a]pyridine

STEP A: Preparation of 3-dimethylaminomethyl-2-methyl-7-(2-phenylethyl)-imidazo[1,2-a]pyridine.

Into a one-liter flask there was placed 2-methyl-7-(2-phenylethyl)-imidazo[1,2-a]pyridine (112 g) dimethylamine hydrochloride (41.6 g), paraformaldehyde (15.23 g) and methanol (450 ml) and the mixture was refluxed with stirring for 1.5 hours. Thereafter the mixture was boiled, open to the air, for ¾ hours. After cooling to room temperature and treatment with concentrated hydrochloric acid (45 ml) the mixture was stirred for 18 hours, filtered and the thick white solid mass formed was washed with methanol and 200 ml of anhydrous ether and dried.

STEP B: Preparation of 3-dimethylaminomethyl-2-methyl-7-(2-phenylethyl)imidazo[1,2-a]pyridine methiodide.

3-dimethylaminomethyl-2-methyl-7-(2-phenylethyl-)imidazo[1,2-a]pyridine hydrochloride (1.325 kg) was dissolved in 4.5 liters of hot water. The solution was made strongly basic with 50% NaOH-solution. The chilled mixture was extracted with dichloromethane (3×1.5 liters) and the combined extracts were washed with brine (1.5 liters). The dichloromethane extract was concentrated on a rotary evaporator. The residual oil was dissolved in 2.5 liters of ethanol. With stirring the solution was cooled and methyl iodide (232 ml) was added dropwise over a period of 1.5 hours. The mixture was allowed to warm to room temperature overnight under continued stirring. The white precipitate was collected after about 18 hours of stirring, washed with 1.5 liters of ethanol and 3 liters of ether. The resulting product is ready for use in Step C below.

STEP C: Preparation of title compound.

A mixture of the methiodide of Step A (1,552 g) and sodium cyanide (310 g) in 8.4 liters of dimethylformamide was stirred and heated in a steam bath for one hour. The dark brown reaction mixture was poured into 30 liters of ice water and the mixture was stirred for one hour. The brown solid product was collected, washed with cold water and allowed to air dry. This material was dissolved in 3.8 liters of hot methanol and treated with hydrogen chloride gas until strongly acidic. The mixture was cooled and the product collected. After washing with methanol, acetonitrile and finally with ether the title product as the hydrochloride salt was obtained.

The salt was re-suspended in water and made strongly alkaline with 10% sodium hydroxide. The product was extracted with dichloromethane (3×2.5 liters) and the combined extracts concentrated on a rotary evaporator. The residue was dissolved in 3.6 liters of hot acetonitrile, and the resulting solution filtered through a glass wool plug and the filtrate was refrigerated overnight. The desired product was then washed with cold acetonitrile (mp 118° C.)

EXAMPLE 33

3-Amino-2-methyl-8-(trans-2-phenylethenyl)-imidazo[1,2-a]pyridine hydrochloride

A. 2-Methyl-8-Formylimidazo[1,2-a]pyridine

A mixture of 2-aminonicotinaldehyde (92.8 g, 0.76 mol) and bromoacetone (114.5 g, 0.84 mol) in dimethoxyethane (980 ml) is stirred for 2 hours at room temperature and then heated at 65° with stirring for 14 hours. The solid which separates is isolated by filtration, dissolved in 800 ml absolute ethanol and heated under a reflux for 6 hours. The ethanol solvent is removed under reduced pressure and the residue treated with 138 ml 6 N hydrochloric acid in 750 ml water for 0.5 hour. The acidic aqueous layer is washed with ether (2×300 ml) and basified with cooling (78 ml) 50% sodium hydroxide and 25 g sodium bicarbonate). The aqueous layer is extracted with dichloromethane. The extracts are combined and dried over anhydrous sodium sulfate. Following filtration, the solvent is removed under reduced pressure to afford 2-methyl-8-formyl-imidazo[1,2-a]pyridine, mp 136°–139.5° C.

B. 2-Methyl-8-hydroxymethylimidazo[1,2pyridine

To a stirred suspension of 56.8 g (0.36 mol) 2-methyl-8-formylimidazo[1,2-a]pyridine in 400 ml isopropanol at 0° is added in portions 8 g (0.21 mol) sodium borohydride. The reaction mixture is stirred at room temperature for an additional 2 hours. The excess sodium borohydride is decomposed by the addition of distilled water and the solution concentrated under reduced pressure at 50° C. The residue is dissolved in water and extracted with chloroform. The chloroform extracts are combined and dried over anhydrous sodium sulfate. Following filtration, the chloroform is removed under reduced pressure to give 2-methyl-8-hydroxymethylimidazo[1,2-a]pyridine.

C. 2-Methyl-8-chloromethylimidazo[1,2-a]pyridine

2-Methyl-8-hydroxymethylimidazo[1,2-a]pyridine 21.4 g (0.13 mol) is dissolved in 400 ml dichloromethane. To the solution at 0° C. is added dropwise with stirring 19 ml of thionyl chloride. The reaction mixture is stirred for one hour and the dichloromethane is removed under reduced pressure. The residue is dissolved in distilled water, neutralized at 0° C. with ammonium hydroxide and extracted with dichloromethane. The extracts are combined and dried over anhydrous sodium sulfate. Following filtration, the dichloromethane is removed under reduced pressure to give 2-methyl-8-chloromethylimidazo[1,2-a]pyridine, mp. 110°–112° C.

D. Diethyl (2-methyl-8-imidazo)[1,2-a]pyridylmethyl)phosphonate

2-Methyl-8-chloromethylimidazo[1,2-a]pyridine 37.7 g (0.21 mol) and 91 ml triethylphosphite are heated together at 145°–150° C. for two hours. Upon cooling, the residue is triturated with petroleum ether and dissolved in ether. Insolubles are removed by filtration and the ether is evaporated under reduced pressure. The oil obtained is dissolved in dichloromethane and dried over anhydrous sodium sulfate. Following filtration, the dichloromethane is removed under reduced pressure to give diethyl (2-methyl-8-imidazo[1,2-a[pyridylmethyl])-phosphonate as an oil.

E. 2-Methyl-8-(2-phenylethenyl)-imidazo[1,2-a]pyridine

A solution of 48.5 g (0.17 mol) diethyl (2-methyl-8-imidazo[1,2-a]pyridylmethyl)phosphonate and 19.4 ml benzaldehyde in 400 ml dimethoxyethane is added dropwise to a stirred suspension of sodium hydride (11.6 g, 0.48 mol) in dimethoxyethane at 0° C.

After stirring overnight, the dimethoxyethane is removed under reduced pressure. The residue is dissolved in water and extracted with dichloromethane. The dichloromethane extracts are combined and dried over anhydrous sodium sulfate. Following filtration, the dichloromethane is removed under reduced pressure. Re-crystallization from ethyl acetate gives 2-methyl-8-(2-phenylethenyl)imidazo[1,2-a]pyridine, mp 101°–105° C.

F. 3-Nitroso-2-methyl-8-(2-phenylethenyl)imidazo[1,2-a]pyridine

To a solution of 5.0 g (0.02 mol) 2-methyl-8-(2-pyenylethenyl)-imidazo[1,2-a]pyridine dissolved in 40 ml acetic acid and 100 ml water at 5° C. is added in portions over 10 minutes, 2.7 g (0.04 mol) sodium nitrite. The mixture is stirred at 0° C. for 20 minutes and at room temperature for 2 hours. Additional water (50 ml) is added, the solid is isolated by filtration and washed thoroughly with distilled water (4×500 ml). Recrystallization from ethyl acetate gives 3-nitroso-2-methyl-8-(2-phenylethenyl)imidazo[1,2-a]pyridine mp 158°–160° C.

G. 3-Amino-2-methyl-8-(2-phenylethenyl)imidazo[1,2-a]pyridine

To a stirred mixture of 3.0 g (0.01 mol) 3-nitroso-2-methyl-8-(2-phenylethenyl)imidazo[1,2-a]pyridine in 50 ml of glacial acetic acid and 50 ml of water at 0° C. is added in portions 3.0 g (0.046 mol) zinc. When the addition is complete the mixture is stirred at 0° C. for 1 hour. The mixture is filtered through celite; the filtrate is diluted with water and dichloromethane and basified at 10° C. with 80 ml of 5 N sodium hydroxide. The resultant emulsion is filtered through a pad of celite and the celite pad is washed thoroughly with hot chloroform. The layers of the filtrate are separated and the aqueous phase is extracted with chloroform. The organic layer is washed with water and brine and dried over anhydrous sodium sulfate.

Following filtration, the chloroform is removed under reduced pressure to give 3-amino-2-methyl-8-(phenylethenyl)-imidazo[1,2-a]pyridine. 1.0 g (0.004 mol) of the free base is dissolbed in ethyl acetate and treated with 2 ml of 3.4 M etheneal hydrogen chloride. Recrystallization of the solid from methanol/ethyl acetate gives, 3-amino-2-methyl-8-(trans-2-phenylethenyl)imidazo[1,2-a]pyridine hydrochloride, mp 241°–250° C. (dec).

EXAMPLE 34

2-Methyl-3-isocyanomethyl-8-phenylmethoxyimidazo[1,2-a]pyridine

2-Methyl-3-formylaminomethyl-8-phenylmethoxyimidazo[1,2-a]pyridine 100 mg (0.29 mmol) is added to 6 ml dichloromethane containing 0.6 ml diisopropyl ethylamine and 0.1 ml phosphorous oxychloride. The mixture is stirred for 2 hours and diluted with water. The dichloromethane layer is separated, washed with saturated sodium bicarbonate, brine and dried over anhydrous magnesium sulfate.

Following filtration the dichloromethane is removed under reduced pressure to give 2-methyl-3-isocyanomethyl-8-phenylmethoxyimidazo[1,2-a]pyridine, m.p.

EXAMPLE 35 trans-2,3-Dimethyl-8-(2-phenylethenyl)imidazo[1,2-a]pyridine hydrochloride

A. 2,3-Dimethyl-8-formylimidazo[1,2-a]pyridine

A solution of 207 g (1.7 mol) 2-aminonicotinaldehyde and 300 g (2.0 mol) 3-bromo-2-butane in 150 ml dichloromethane is heated on a steam bath allowing the solvent to distill and the mixture is maintained at 100°–105° C. for 2 hours.

The reaction mixture is dissolved in dilute hydrochloric acid and extracted with ether. The aqueous layer is neutralized with 20% sodium hydroxide. The solid precipitate is isolated by filtration and recrystallized from ethyl acetate to give 2,3-dimethyl-8-formylimidazo[1,2-a]pyridine, mp 145°–148° C.

B. trans-2,3-dimethyl-8-(2-phenylethenyl)imidazo[1,2-a]pyridine hydrochloride

A stirred solution of 116 g (0.51 mol) diethylbenzylphosphonate in 300 ml dimethylformamide is treated with 28 g (0.052 mol) sodium methoxide.

2,3-Dimethyl-8-formylimidazo[1,2-a]pyridine (80 g, 0.46 mol) is added in portions over 35 minutes while maintaining the temperature between 30°–35° C. After stirring at room temperature 2.5 hours, the solvent is removed under reduced pressure and the residue partitioned between 300 ml dichloroethane and 500 ml water.

The dichloromethane layer is separated and the solvent is removed under reduced pressure. The solid is triturated with ether (3×100 ml) and insolubles are removed from the ether solutions by filtration. The ether filtrates are combined and treated with ethereal hydrogen chloride. Recrystallization of the solid from water gives trans-2,3-dimethyl-8-(2-phenylethenyl)imidazo[1,2-a]pyridine, mp. 240°–255° C.

EXAMPLE 36

2,7-dimethyl-8-phenylmethoxyimidazo[1,2a]pyridin-3-acetonitrile

A: 2-amino-3-phenylmethoxy-4-methlylpyridine was prepared as an oil by reacting 2-amino-3-hydroxy-4-methylpyridine with benzyl chloride following the procedures of Example 1, Step A herein.

B: The Title compound (mp 82°–83°) was prepared by reacting 2-amino-3-phenylmethoxy-4-methylpyridine with 3-chloro-4-oxopentanonitrile following the procedure of Example 2, Step B herein.

One may be following the appropriate process of those disclosed herein and exemplified above, prepare all further compounds falling within the scope of this invention such as those shown in the following Table II.

TABLE II

| $R_2$ | $R_3$ | $R_4$ | $R_5$ |
|---|---|---|---|
| —CH$_3$ | —CH$_2$OH | 8-(3,4-dichlorobenzyloxy) | H |
| —CH$_3$ | —CH$_2$OH | 8-(4,t-butylbenzyloxy) | H |
| H | —CH$_2$CN | 8-benzyloxy | H |

TABLE II-continued

| $R_2$ | $R_3$ | $R_4$ | $R_5$ |
|---|---|---|---|
| —CH₃ | —CH₂CN | 8-(4-chlorobenzyloxy) | H |
| —CH₃ | H | 8-(2-phenylethoxy) | H |
| —CH₃ | —CH₃ | 8-benzyloxy | H |
| —CH₃ | H | 8-(2-phenylethyl) | H |
| —CH₃ | —CH₂CN | 8-(4-t-butylbenzyloxy) | H |
| —C(CH₃)₃ | H | 8-benzyloxy | H |
| —CH₃ | H | 8-(4-t-butylbenzyloxy) | H |
| —CH₃ | —CH₂CN | 8-(1-phenylethoxy) | H |
| —CH₃ | —CH₂CN | 8-phenylethyl | H |
| —CH₃ | —CH₂CN | 8-benzyloxy | 5-CH₃ |
| —CH₃ | H | 8-(2,4,6-trimethylbenzyloxy) | H |
| —CH₃ | —CH₂OH | 8-phenylethyl | H |
| —CH₃ | —CH₂CN | 8-(2,4,6-trimethylbenzyloxy) | H |
| —CH₃ | —CH₂CH₃ | 8-benzyloxy | |
| —CH₂OH | H | 8-benzyloxy | H |
| —CH₃ | H | 8-(2-pyridylmethoxy) | H |
| —CH₃ | —CH₂CN | 8-(3-pyridylmethoxy) | H |
| —CH(CH₃)₂ | H | 8-benzyloxy | H |
| —CH₃ | —CH₂CN | 8-benzyloxy | 6-Cl |
| —CH₂—CH₃ | H | 8-benzyloxy | H |
| —CH₂—CH₃ | —CH₂CN | 8-benzyloxy | H |
| —CH₃ | —CH₂CN | 8-(phenylpropyloxy) | H |
| —CH₃ | —CH₃ | 8-benzylamino | H |
| —CH₃ | —CH₂CN | 8-(3-thienylmethoxy) | H |
| —CH₃ | —CH₂CN | 8-(4-pyridylmethoxy) | H |
| —C₂H₅ | —CH₃ | 8-benzyloxy | H |
| —CH₃ | H | 8-benzylaminomethyl | H |
| —CH₃ | —CH₂CN | 8-(2-furanyl)methylamino | H |
| —CH₃ | —CH₂CN | 8-(3-furanyl)methoxy | H |

As is also obvious to anyone skilled in the art, the respective $R_5$ substituted analogues of the $R_5$-substituted compounds in the above Table and in the Examples may also be obtained by the processes above by using the appropriate $R_5$-substituted starting compounds.

The compounds of this invention are useful in the treatment of peptic ulcers. They display chemotherapeutic activity which enables them to relive the symptoms of peptic ulcer disease, including stress ulceration, and promote healing of gastric and/or duodenal ulcers. The anti-ulcer activity of the compounds of this invention is identified by tests which measure their gastric antisecretory activity in the rat and dog and by tests which measure their cytoprotective effect (sometimes also referred to in the art as mucoprotective effect) in rats. The compounds are also useful as conjunctive therapeutic agents for coadministration with such anti-inflammatory/analgesic agents as aspirin, indomethacin, phenylbutazone, ibuprofen, naproxen, tolmetin and other agents having the untoward side effect of contributing irritation and damage to the gastrointestional tract.

The compounds of this invention are evaluated for their activity characteristics by standard biological testing procedures. In the testing procedures the compounds are evaluated both on an absolute basis and on a comparative basis with compounds known to possess the activity useful for the treatment and/or prevention of peptic ulcer disease, duodenal ulcer disease and drug induced gastric ulceration. Such tests include testing in dogs prepared under aseptic surgical conditions with either Heidenhain gastric pouches or simple gastric fistulas fitted to facilitate collection of gastric secretions. The test compounds are administered in appropriate and well-defined and well-known vehicles for either intravenous delivery or oral administration. The agonists employed to stimulate gastric secretion include such compounds as histamine, pentagastrin, and feeding in dogs equipped with Heidenhain pouches, and insulin hypoglycemia (in addition to histamine and pentagastrin) in dogs with gastric fistulas.

Caesarean-derived Sprague-Dawley male rats are used for gastric secretion with pyloric ligation techniques and anti-ulcer studies employing asprin-induced ulceration.

In cytoprotective tests in rats in which ethanol is employed to induce gastrointestional damage, the compounds of this invention are found to be effective for the oral treatment of the ulcerative disease states mentioned herein.

From these and other tests, as well as by comparision with known anti-ulcer agents the compounds of this invention are found to be effective for the oral treatment of the ulcerative disease states herein mentioned at doses of about 0.5 to 50 mgm per kilogram of body weight per day. Preferably the total dosages are administered in 2–4 divided doses per day. In those instances wherein it is desired to administer the compounds of this invention via a parenteral route (e.g. intravenously) the compounds are administered at a dose range of about 0.01 to 10 mg/kg in single or multiple daily doses. Of course, the dose will be regulated according to the judgment of the attending diagnostician depending on factors such as the degree and severity of the disease state and age and general condition of the patient being treated. The recommended dose range for the preferred compounds of this invention is an oral dose of 75 to 1600 mg/day preferable 600 to 800 mg per day in two to four divided doses to achieve relief of the symptoms of peptic ulcer disease and promote the healing of gastric and/or duodenal ulcers.

In their use in the treatment of peptic ulcer disease, gastric and duodenal ulcers, and in the prevention and treatment of drug-induced gastric ulceration, the compounds of this invention are administered in unit dosage forms such as tablets, capsules, pills, powders, granules, sterile parenteral solutions or suspensions, suppositories, mechanical delivery devices, e.g. transderman, and the like. Such dosage forms are prepared according to standard techniques well known in the art. A few examples of such pharmaceutical formulations are as follows.

FORMULATIONS

The following formulations are to exemplify some of the dosage forms in which the anti-ulcer agents of this invention may be employed. In each, the active ingredient is designated by the term "Drug" which is meant to indicate one of the following compounds:

2,7-dimethyl-8-phenymethoxyimidazo[1,2-a]pyridine-3-acetonitrile 2-methyl-8-phenylmethoxyimidazo[1,2-a]pyridine-3-acetonitrile; and 2-methyl-8-benzylaminoimidazo[1,2-a]pyridine-3-acetonitrile.

It will be appreciated, however, that each of these compounds may be replaced by equally effective quantities of other compounds of this invention.

| | Formulation 1 Tablets | | |
|---|---|---|---|
| No. | Ingredient | mg/tab | mg/tab |
| 1 | Drug | 25.0 | 400.0 |
| 2 | Lactose, impalpable powder USP | 114.0 | 241.5 |
| 3 | Corn starch USP | 25.0 | 50.0 |
| 4 | Corn starch as 5% paste in distilled water | 10.0 | 35.0 |

| Formulation 1 Tablets | | | |
|---|---|---|---|
| No. | Ingredient | mg/tab | mg/tab |
| 5 | Corn starch USP | 25.0 | 50.0 |
| 6 | Magnesium Stearate USP | 1.0 | 3.5 |
| | | 200.0 | 780.0 |

METHOD OF MANUFACTURE

Mix items nos. 1, 2 and 3 in a suitable blender for 5 to 15 minutes. Pass through a fine screen (#40) if necessary. Reblend for 5 to 10 minutes and granulate with item no. 4. Pass the damp granulated mass through a coarse sieve (#6) using a suitable mill. Dry the damp granules at 40° to 50° oernight. Mill the dried granules using a no. 20 screen. Add item no. 5 and blend for 5 to 10 minutes. Add item no. 6 and blend further for 3 to 5 minutes. Compress the tablet mixture into tablets of an appropriate size and weight using a suitable tableting machine.

| Formulation 2 Capsules | | | |
|---|---|---|---|
| No. | Ingredient | mg/tab | mg/tab |
| 1 | Drug | 25.0 | 400.0 |
| 2 | Lactose, impalpable powder USP | 144.0 | 191.5 |
| 3 | Corn starch USP | 30.0 | 105.0 |
| 4 | Magnesium Stearate USP | 1.0 | 3.5 |
| | | 200.0 | 700.0 |

METHOD OF MANUFACTURE

Mix items nos. 1, 2 and 3 in a suitable blender for 5 to 10 minutes. Pass through a fine screen (#40) if necessary. Reblend for 5 to 10 minutes, add item no. 4 and mix further for 3 to 50 minutes. Using a suitable machine, encapsulate the mixture into a two-piece hard gelatin capsule of appropriate size.

| Formulation 3 Suspensions | | |
|---|---|---|
| Ingredients | Formula A (mg/ml) | Formula B (mg/ml) |
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

Method of Manufacture

1. Charge approximately 40% of the final volume of purified water in a stainless steel tank. Heat to boiling. Agitate using an appropriate stirrer. Agitation should continue throughout procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.
7. Dilute the suspension to final volume with purified water at 25°.

| Formulation 4 Parenteral | |
|---|---|
| | mg/ml |
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

Method of Manufacture

1. Dissolve parabens in a portion (approximately 85% of the final volume) of the water for injection at 65–70°.
2. Cool to 25–35°. Charge and dissolve sodium bisulfite, disodium edetate and sodium sulfate.
3. Charge and dissolve the Drug.
4. Bring the solution to the final volume by adding water for injection.
5. Filter the solution through a 0.22-micron membrane and fill into appropriate containers.
6. Terminally sterilize the units by autoclaving.

| Formulation 5 Injectable Suspension | |
|---|---|
| | mg/ml |
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

Method of Preparation

1. Dissolve parabens in a portion of water for injection at 65–70°.
2. Cool to 25–35°. Charge and dissolve benzyl alcohol, sodium citrate, disodium edetate, PEG 4000, povidone and sodium carboxymethylcellulose.
3. Filter the solution and sterilize by autoclaving.
4. Make a slurry of the sterile Drug and pass it through a colloid mill.
5. Mix it well with solution from Step 3 and pass it through the mill.
6. Bring the suspension to the final volume/weight and fill into sterile containers.

| Formulation 6 Suppositories | | |
|---|---|---|
| A. | Formula | mg/supp |
| | Drug | 5.0 |
| | Cocoa butter | 1995.0 |
| | | 2000.0 mg (2.0 g.) |

Procedure

1. Melt cocoa butter to about 32–35°.
2. Blend Drug into cocoa butter until well dispersed.
3. Pour into teflon-coated mold and congeal in refrigerator. Keep in refrigerator for an appropriate length of time.
4. Remove suppositories from mold.

| B. | Formula | mg/supp |
|---|---|---|
| | Drug | 100.0 |
| | PEG 1000 | 1824.0 |
| | PEG 4000 | 76.0 |
| | | 2000.0 mg |

-continued

| Formulation 6 |
| --- |
| Suppositories |
| (2.0 g.) |

Procedure
1. Melt PEG 1000 and PEG 4000 in one container to 50°.
2. Add Drug to mixture. Blend until well dispersed.
3. Pour into mold and congeal in refrigerator. Keep in refrigerator for an appropriate length of time.
4. Remove suppositories from mold.

Since all the compounds within the large class of compounds encompassed by this invention are not equally therapeutically potent, certain subgroups and certain specific compounds have been found to be preferred for their therapeutic utility. Preferred are those compounds having the imidazo[1,2-a]pyridine nucleus containing an oxygen or nitrogen linkage at the 8-position. Another preferred group is where "Ar" represents phenyl or 3-thienyl. Still another preferred group contains the "Ar" moiety linked to the 8-position of the imidazo[1,2-a]pyridine nucleus either through a methoxy, ethoxy, methylamino or ethylamino, i.e., wherein T represents methylene or ethylene; or directly through an ethylene, ethenylene or propenylene. Another preferred group is composed of compounds containing an alkyl moiety, particularly methyl, at the 2-position and an acetonitrile or amino radical at the 3-position. Another preferred group are those compounds having a hydroxyalkyl at the 2- or 3-position. Preferred specific compounds include those imidazo[1,2-a]pyridines having the following substituents:

| $R_2$ | $R_3$ | $R_4$ | $R_5$ |
| --- | --- | --- | --- |
| $CH_3$ | $CH_2CN$ | $-O-CH_2-$phenyl | (7)$CH_3$ |
| $CH_3$ | $CH_3$ | $-CH=CH-$phenyl | H |
| $CH_3$ | $CH_2CN$ | $-CH=CH-CH_2-$phenyl | H |
| $CH_3$ | $NH_2$ | $-CH_2CH_2-$phenyl | H |
| $CH_3$ | $NH_2$ | $-O-CH_2-$(3-thienyl) | H |
| $CH_3$ | $CH_2NC$ | $-O-CH_2-$phenyl | H |
| $CH_3$ | $NH_2$ | $-NH-CH_2-$(3-thienyl) | H |
| $CH_3$ | $NH_2$ | $-O-CH_2-$(2-thienyl) | H |
| $CH_3$ | $NH_2$ | $-O-CH_2(4$-chloro)phenyl | H |
| $CH_3$ | $NH_2$ | $-O-CH_2-$(2-fluoro)phenyl | H |
| $CH_3$ | $NH_2$ | $-O-CH_2-$phenyl | (7)$CH_3$ |
| $CH_3$ | $NH_2$ | $-O-CH_2-$phenyl | (6)$CH_3$ |
| $CH_2CH_3$ | $NH_2$ | $-O-CH_2-$phenyl | H |
| $CH_3$ | $NH_2$ | $-NH-CH_2-$phenyl | H |
| $CH_3$ | $NHCH_2CH_3$ | $-CH_2-CH_2-$phenyl | H |
| $CH_3$ | $NHCH_2CH_3$ | $-O-CH_2-$phenyl | H |
| $CH_3$ | $NH_2$ | $-OCH_2(4$-fluoro)phenyl | H |
| $CH_3$ | $CH_2CN$ | $-NH-CH_2-$(3-thienyl) | H |
| $CH_3$ | $CH_2CN$ | $-O-CH_2-$phenyl | H |
| $CH_3$ | $CH_2CN$ | $-O-CH_2H_2-$phenyl | H |
| H | $CH_2CN$ | $-O-CH_2-$phenyl | H |
| $CH_3$ | $CH_2CN$ | $-O-CH_2-$(4-chloro)phenyl | H |
| $CH_2OH$ | $CH_2CN$ | $-O-CH_2-$phenyl | H |
| $CH_3$ | $CH_2CN$ | $-O-CH_2-$(2-fluoro)phenyl | H |
| $CH_3$ | $CH_2CN$ | $-O-CH_2-$(4-fluoro)phenyl | H |
| $CH_3$ | $CH_2CN$ | $-O-CH_2-$thienyl | H |
| $CH_3$ | $NH_2$ | $-O-CH_2-$phenyl | H |
| $CH_3$ | $CH_2OH$ | $-O-CH_2-$phenyl | H |
| $CH_3$ | $CH_2OH$ | $-O-CH_2-$(2-fluoro)phenyl | H |
| $CH_3$ | $CH_2CN$ | $-NH-CH_2-$phenyl | H |
| $CH_3$ | $CH_2CN$ | $-O-CH_2-$phenyl | (5)$CH_3$ |
| $CH_3$ | $CH_2CN$ | $-O-CH_2-$phenyl | (6)Cl |
| $CH_3$ | $CH_2CN$ | $-CH_2-CH_2-$phenyl | H |
| $CH_3$ | $CH_3$ | $-O-CH_2-$phenyl | H |
| $CH_3$ | H | $-O-CH_2-$phenyl | H |

We claim:
1. A compound represented by the formula

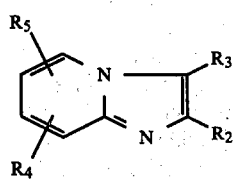

and the 2,3-dihydro,5,6,7,8-tetrahydro and 2,3,5,6,7,8-hexahydro derivatives thereof, and the pharmaceutically acceptable salts thereof, wherein:
$R_2$ is hydrogen, lower alkyl or hydroxyloweralkyl;
$R_3$ is lower alkyl, $-CH_2CN$, hydroxyloweralkyl, $-NO$, $-CH_2N=C$ or

(wherein $R_6$ and $R_7$ are independently selected from the group consisting of hydrogen and lower alkyl) or hydrogen, provided $R_2$ is not hydrogen;
$R_4$ is Z-T-W wherein Z represents $-O-$, $-NH-$ or a single bond; T represents a straight or branched chain lower alkylene group and when Z is a single bond, T also represents an ethenylene or a propenylene group wherein the unsaturated carbon is at the single bond and when Z is $-O-$, T also represents an allylene group wherein the saturated carbon is at the oxygen;
W represents Ar and when T is allylene and Z is $-O-$, W represents hydrogen;
Ar represents thienyl, pyridinyl, furanyl, phenyl and substituted phenyl wherein there are one or more substituents on the phenyl independently selected from halogen or lower alkyl; and
$R_5$ is hydrogen, halogen or lower alkyl.
2. A compound of claim 1 wherein $R_2$ is methyl or ethyl;
$R_3$ is $-NH_2$, $-NHC_2H_5$, $-CH_2CN$, $-CH_3$, $-CH_2OH$ or $-CH_2NC$;
$R_4$ is $-OCH_2Ar$, $-CH=CH-(CH_2)_n$ Ar or $-CH_2CH_2(CH_2)_nAr$ wherein n is zero or one and Ar is as defined in claim 1; and
$R_5$ is hydrogen, fluoro, chloro or methyl.
3. A compound of claim 1 wherein $R_4$ is at the 8-position.
4. A compound of claim 3 wherein $R_4$ is phenylmethoxy, phenylethyl, 3-phenyl-1-propenyl, phenylethenyl, benzylamino, 3-thienylmethoxy or 3-thienylmethanamino.
5. A compound of claim 4 wherein:
$R_2$ is methyl;
$R_3$ is amino, cyanomethyl or methyl;
$R_5$ is hydrogen or methyl.
6. A compound of claim 1 which is 2-methyl-6-benzylaminoimidazo[1,2-a]pyridine-3-acetonitrile.
7. A compound of claim 1 which is 2-methyl-6-benzyloxyimidazo[1,2-a]pyridine-3-acetonitrile.
8. A compound of claim 1 which is 2-methyl-5-benzylaminoimidazo[1,2-a]pyridine-3-acetonitrile.
9. A compound of claim 1 which is 2-methyl-5-benzyloxyimidazo[1,2-a]pyridine-3-acetonitrile.
10. A compound of claim 1 which is 2,3-dimethyl-5-benzyloxyimidazo[1,2-a]pyridine.

11. A compound of claim 1 which is 2-methyl-7-benzyloxyimidazo[1,2-a]pyridine-3-acetonitrile.

12. A compound of claim 1 which is 2-methyl-7-benzylaminoimidazo[1,2-a]pyridine-3-acetonitrile.

13. A compound of claim 3 which is 2-methyl-8-benzyloxyimidazo[1,2-a]pyridine-3-acetonitrile.

14. A compound of claim 3 which is 2-methyl-8-phenylethoxyimidazo[1,2-a]pyridine-3-acetonitrile.

15. A compound of claim 3 which is 8-benzyloxyimidazo[1,2-a]pyridine-3-acetonitrile.

16. A compound of claim 3 which is 2-methyl-8-(4-chlorophenyl)methoxyimidazo[1,2-a]pyridine-3-acetonitrile.

17. A compound of claim 3 which is 2-hydroxymethyl-8-benzyloxyimidazo[1,2-a]pyridine-3-acetonitrile.

18. A compound of claim 3, said compound being 2-methyl-8-(2-fluorophenyl)methoxyimidazo[1,2-a]pyridine-3-acetonitrile.

19. A compound of claim 3 which is 2-methyl-8-(4-fluorophenyl)methoxyimidazo[1,2-a]pyridine-3-acetonitrile.

20. A compound of claim 3 which is 2-methyl-8-(2-fluorophenyl)methoxyimidazo[1,2-a]pyridine-3-methanol.

21. A compound of claim 3 which is 2-methyl-8-(3-thienyl)methoxyimidazo[1,2-a]pyridine-3-acetonitrile.

22. A compound of claim 3 which is 2-methyl-8-(2-thienyl)methoxyimidazo[1,2-a]pyridine-3-acetonitrile.

23. A compound of claim 3 which is 8-benzyloxy-2,7-dimethylimidazo[1,2-a]pyridine-3-acetonitrile.

24. A compound of claim 3 which is 2-methyl-8-benzylaminoimidazo[1,2-a]pyridine-3-acetonitrile.

25. A compound according to claim 3 which is 2-methyl-8-(3-thienyl)methylaminoimidazo[1,2-a]pyridine-3-acetonitrile.

26. A compound of claim 1 wherein $R_4$ is allyloxy.

27. A compound of claim 26 which is 2-methyl-8-allyloxyimidazo[1,2-a]pyridine-3-acetonitrile.

28. A compound of claim 3 which is 8-benzyloxy-2-ethylimidazo[1,2-a]pyridine-3-acetonitrile.

29. A compound of claim 3 which is 3-amino-2-methyl-8-benzyloxyimidazo[1,2-a]pyridine.

30. A compound of claim 3 which is 3-amino-2-methyl-8-phenylethylimidazo[1,2-a]pyridine.

31. A compound of claim 3 which is 3-nitroso-2-methyl-8-phenylmethoxyimidazo[1,2-a]pyridine.

32. A compound of claim 4 which is 2,3-dimethyl-trans(8-phenylethenyl)imidazo[1,2-a]pyridine.

33. A compound of claim 3 which is 2-methyl-8-(trans 3-phenyl-1-propenyl)-imidazo[1,2-a]pyridine-a-acetinitrile.

34. A compound of claim 3 which is 3-nitroso-2-methyl-8-phenylethylimidazo[1,2-a]pyridine.

35. A method for the treatment of the symptoms of peptic ulcer disease in mammals, which comprises administering to a mammal having peptic ulcer disease a therapeutically effective quantity of a compound of claim 1.

36. A method for the treatment of gastric ulcers in mammals which comprises administering to a mammal having gastric ulcers a therapeutically effective quantity of a compound of claim 1.

37. A method for the treatment of duodenal ulcers in mammals which comprises administering to a mammal having duodenal ulcers a therapeutically effective quantity of a compound of claim 1.

38. A method for inhibiting the formation of gastrointestinal irritation and damage in mammals due to drug-induced gastrointestinal irritation and damage which comprises administering a therapeutically effective amount of a compound of claim 1 during the term said gastrointestinal irritating and damaging drug is administered for its therapeutic effect.

39. A method for the treatment of gastrointestinal damage due to stress which comprises administering to a mammal suffering from such damage a therapeutically effective quantity of a compound of claim 1.

40. A pharmaceutical formulation for use in the treatment of ulcers which comprises a compound of claim 1 in a therapeutically effective amount sufficient to alleviate the symptoms of peptic ulcer disease together with a non-toxic, pharmaceutically acceptable carrier.

41. A pharmaceutical formulation of claim 40 comprising a therapeutically effective amount of 2-methyl-8-benzyloxyimidazo[1,2-a]pyridine-3-acetonitrile together with a non-toxic pharmaceutically acceptable carrier.

42. A pharmaceutical formulation of claim 40 comprising a therapeutically effect amount of 8-benzyloxy-2,7-dimethylimidazo[1,2-a]pyridine-3-acetonitrile.

* * * * *